(12) United States Patent
Wehlin et al.

(10) Patent No.: US 10,465,835 B2
(45) Date of Patent: Nov. 5, 2019

(54) PIPE TRAVERSING APPARATUS AND METHODS

(71) Applicant: ARIX TECHNOLOGIES, INC., New Haven, CT (US)

(72) Inventors: Karl Petter Wehlin, Houston, TX (US); Bryan R. Duerfeldt, Houston, TX (US); Dianna D. Liu, Jackson, LA (US); Gary E. van Deursen, Essex, CT (US); Timothy D. Foldy-Porto, Northampton, MA (US)

(73) Assignee: Arix Technologies, Inc., Jackson, LA (US)

( * ) Notice: Subject to any disclaimer, the term of this patent is extended or adjusted under 35 U.S.C. 154(b) by 0 days.

(21) Appl. No.: 16/135,413

(22) Filed: Sep. 19, 2018

(65) Prior Publication Data
US 2019/0086020 A1 Mar. 21, 2019

Related U.S. Application Data

(60) Provisional application No. 62/560,265, filed on Sep. 19, 2017, provisional application No. 62/616,147, (Continued)

(51) Int. Cl.
*F16L 55/34* (2006.01)
*B25J 9/16* (2006.01)
(Continued)

(52) U.S. Cl.
CPC .............. *F16L 55/34* (2013.01); *B25J 5/007* (2013.01); *B25J 5/02* (2013.01); *B25J 9/1664* (2013.01);
(Continued)

(58) Field of Classification Search
CPC ...... G01N 2223/628; G01N 2291/2634; F16L 55/18; F16L 55/26; F16L 55/28;
(Continued)

(56) References Cited

U.S. PATENT DOCUMENTS

| | | | | |
|---|---|---|---|---|
| 4,531,413 A | * | 7/1985 | Tsuchita | ............... B82Y 15/00 |
| | | | | 73/637 |
| 5,686,668 A | * | 11/1997 | McLean | ............... B21C 51/00 |
| | | | | 73/622 |

(Continued)

FOREIGN PATENT DOCUMENTS

KR 20130034257 A 4/2013

OTHER PUBLICATIONS

International Search Report in corresponding International Patent Application No. PCT/US2018/051723 dated Nov. 14, 2018.

*Primary Examiner* — Zachary L Kuhfuss
(74) *Attorney, Agent, or Firm* — Greenberg Traurig LLP; Todd C. Basile; David J. Dykeman

(57) ABSTRACT

A robotic apparatus comprising first, second, and third wheel assemblies, and a clamping mechanism configured to apply a force for urging the second wheel and the third wheel to pivot in opposing directions towards a plane of the first wheel for securing the first wheel, the second wheel, and the third wheel to the pipe, each wheel assembly including an alignment mechanism for adjusting an orientation of the wheels to allow the robotic apparatus to move along a straight path or a helical path on the pipe. A method for navigating an obstacle on a pipe comprising advancing the robotic apparatus along a helical pathway on the pipe to position an open side of the robotic apparatus in longitudinal alignment with the obstacle, and advancing the robotic
(Continued)

apparatus along a straight pathway on the pipe such that the obstacle passes unobstructed through the open side of the robotic apparatus.

24 Claims, 31 Drawing Sheets

Related U.S. Application Data filed on Jan. 11, 2018, provisional application No. 62/687,753, filed on Jun. 20, 2018.

(51) Int. Cl.
| | |
|---|---|
| *B25J 5/00* | (2006.01) |
| *B25J 5/02* | (2006.01) |
| *B60K 1/00* | (2006.01) |
| *G01N 29/22* | (2006.01) |
| *G01N 29/265* | (2006.01) |
| *B25J 13/08* | (2006.01) |
| *F16L 55/18* | (2006.01) |
| *F16L 101/30* | (2006.01) |

(52) U.S. Cl.
CPC ............... *B25J 9/1679* (2013.01); *B60K 1/00* (2013.01); *G01N 29/225* (2013.01); *G01N 29/265* (2013.01); *B25J 13/085* (2013.01); *F16L 55/18* (2013.01); *F16L 2101/30* (2013.01); *G01N 2291/2634* (2013.01)

(58) Field of Classification Search
CPC ........ F16L 55/34; F16L 2101/30; B25J 5/007; B25J 5/02; B25J 9/1664; B25J 9/1679; B25J 13/085
USPC ................... 73/622, 638; 104/138.2; 378/59
See application file for complete search history.

(56) References Cited

U.S. PATENT DOCUMENTS

| | | | |
|---|---|---|---|
| 5,698,854 A | 12/1997 | Gupta | |
| 7,594,448 B2 * | 9/2009 | Jacobson | G05D 1/0891 73/865.8 |
| 7,656,997 B1 * | 2/2010 | Anjelly | G01N 23/04 378/59 |
| 8,141,442 B2 * | 3/2012 | Roberts | F17D 5/00 73/865.8 |
| 8,759,780 B2 * | 6/2014 | Dobbs | G01B 15/02 250/360.1 |
| 9,366,596 B2 | 6/2016 | Mekid et al. | |
| 9,726,569 B2 * | 8/2017 | Koyanagi | G01N 23/025 |
| 2018/0011064 A1 * | 1/2018 | Furr | G01N 29/30 |
| 2018/0284074 A1 * | 10/2018 | Furr | G01N 29/30 |
| 2019/0086020 A1 * | 3/2019 | Wehlin | F16L 55/34 |
| 2019/0120418 A1 * | 4/2019 | Sivacoe | B08B 9/049 |

* cited by examiner

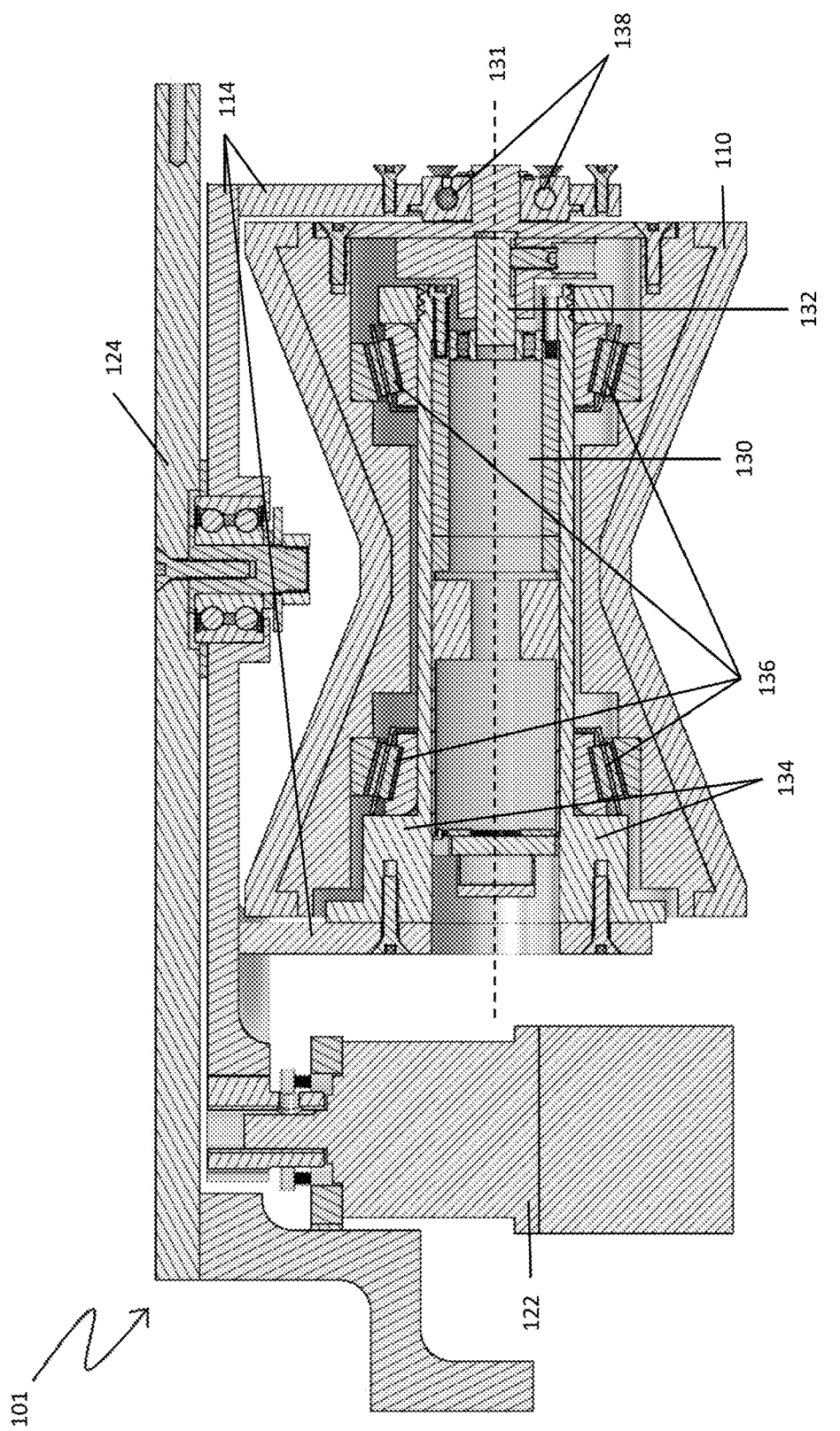

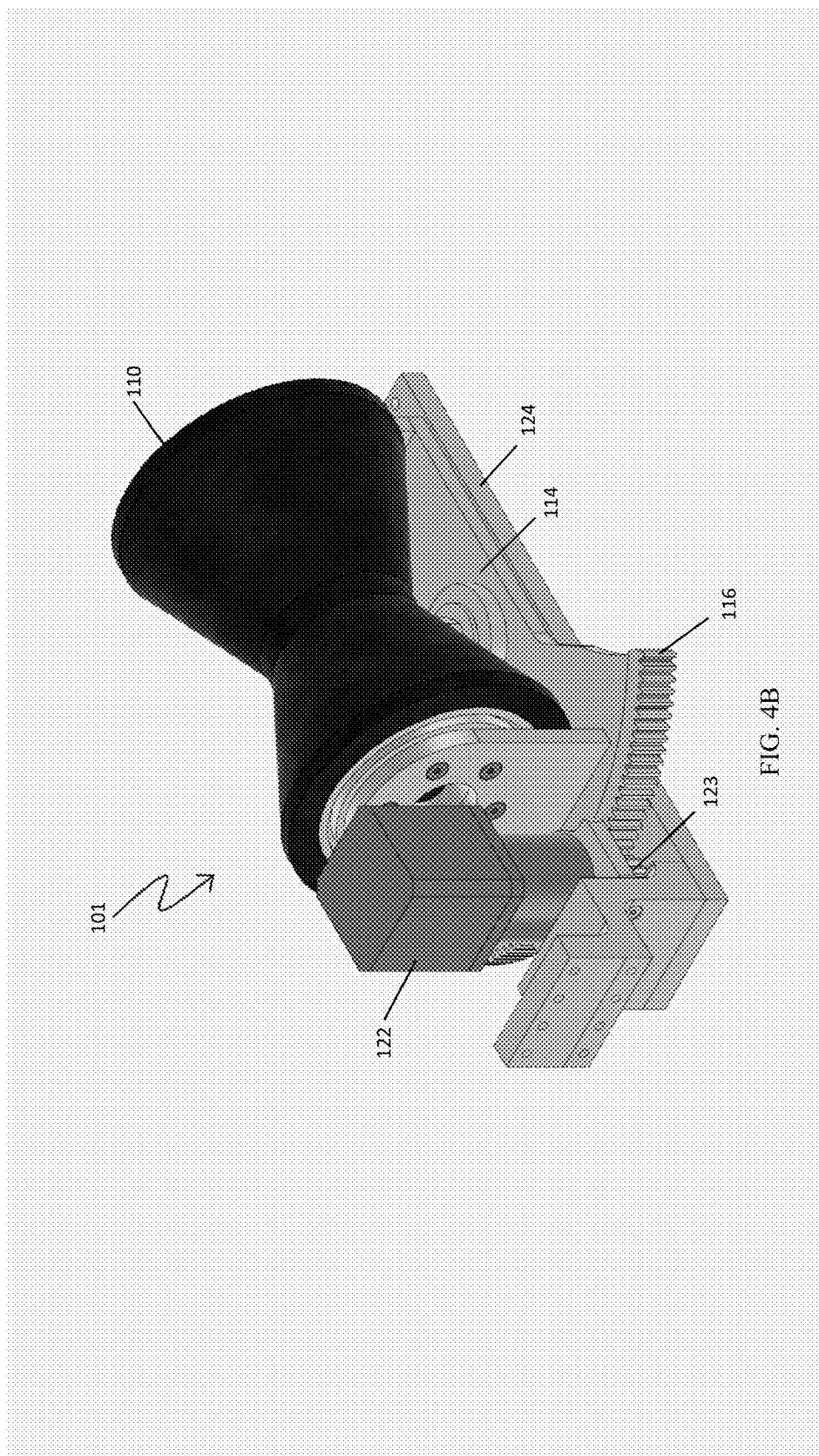

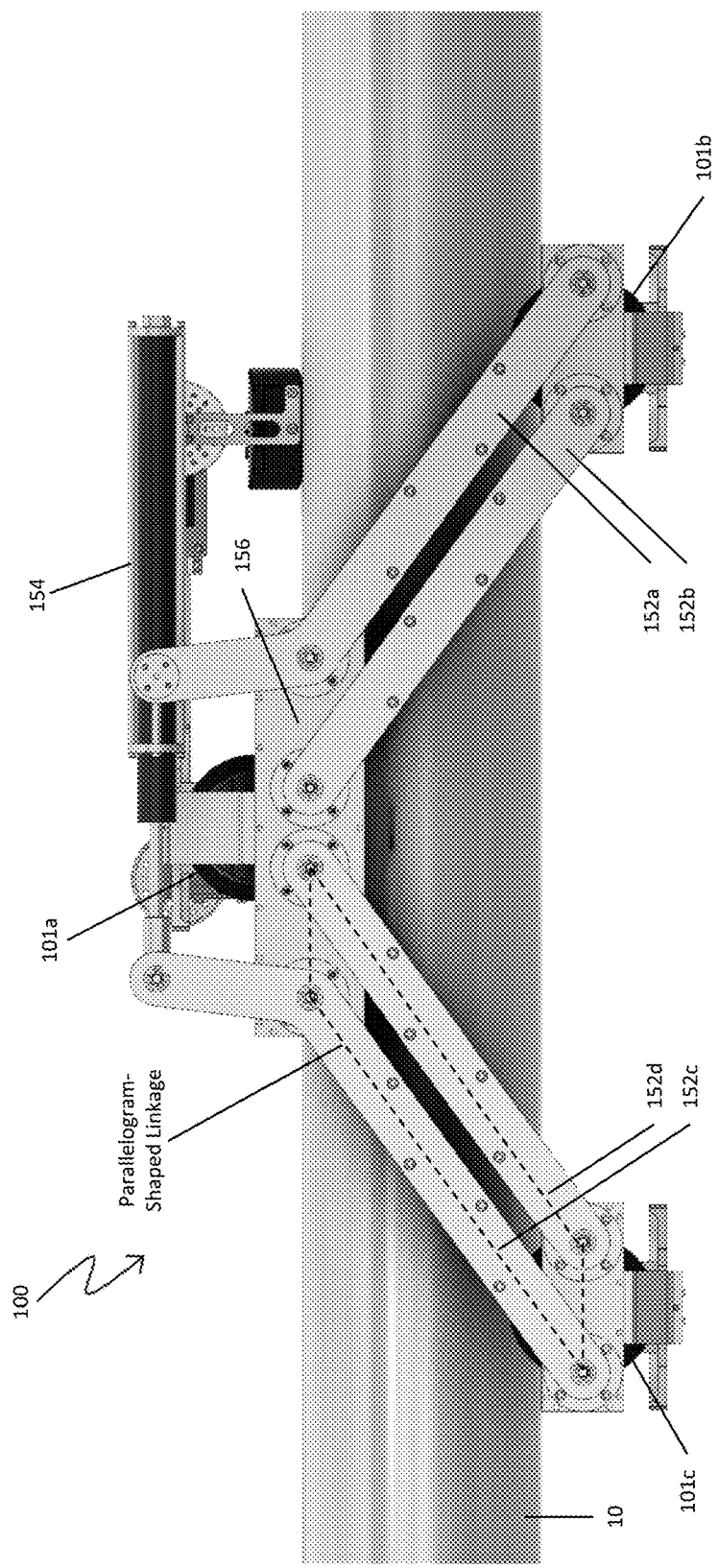

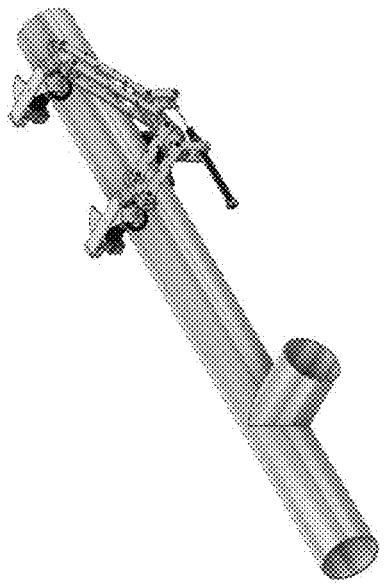
FIG. 9A
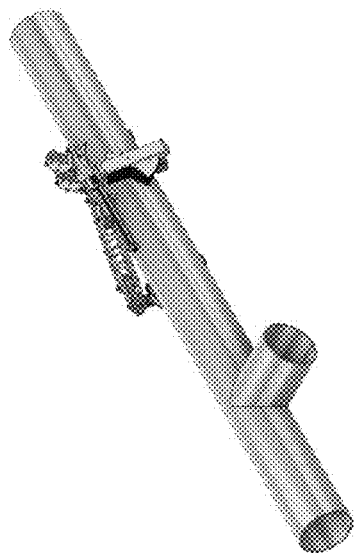
FIG. 9B
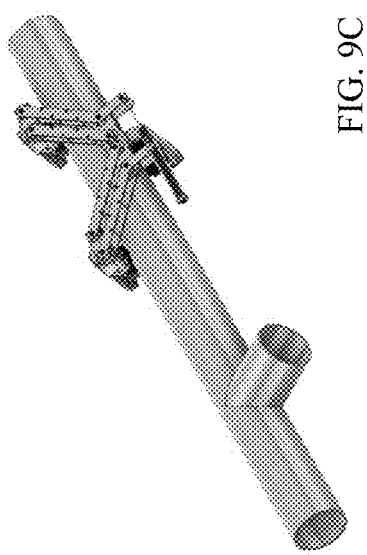
FIG. 9C
FIG. 9D

PIPE TRAVERSING APPARATUS AND METHODS

CROSS-REFERENCE TO RELATED APPLICATION(S)

This application claims the benefit of and priority to U.S. Provisional Application No. 62/560,265, filed Sep. 19, 2017, U.S. Provisional Application No. 62/616,147, filed Jan. 11, 2018, and U.S. Provisional Application No. 62/687,753, filed Jun. 20, 2018, all of which are hereby incorporated herein by reference in its entirety for all purposes.

BACKGROUND

Many existing pipe crawling apparatuses are designed to either travel inside of pipes or are not equipped to travel around obstacles it may encounter on the outside of pipes. In view of limitations of current technologies, a need remains for pipe-crawling apparatus that are effective in navigating around and/or over potential obstacles, e.g., obstacles that present a change in the effective diameter of the pipe, a change in the effective curvature of the pipe, and/or obstacles that protrude from the pipe in one or more radial directions. More particularly, pipe-crawling apparatus are needed that are effective in navigating around and/or over flanges, valves, tees, bends, supports and the like. In addition, a need remains for pipe-crawling apparatus that are effective in traveling relative to pipes without magnets, vacuum or aerodynamic forces. Additionally, a need remains for pipe-crawling apparatus and associated systems that are effective in performing desired functions relative to the pipe itself, e.g., corrosion detection, wall thickness measurements, or based on travel along the path but independent of the pipe itself, e.g., imaging and/or sensing of locations accessible through travel along a pipe. These and other needs are advantageously satisfied by the apparatus and systems disclosed herein.

SUMMARY

The present disclosure is directed to a robotic apparatus for traversing the outer surface a pipe or similar structure. The robotic apparatus, in various embodiments, may comprise a first wheel assembly including a wheel and an alignment mechanism, and configured for positioning on a first side of a pipe; a second wheel assembly and a third wheel assembly, each including a wheel and an alignment mechanism, and configured for positioning on a second, opposing side of the pipe; and a clamping mechanism configured to apply a force for urging the second wheel and the third wheel to pivot in opposing directions towards a plane of the first wheel for securing the first wheel, the second wheel, and the third wheel to the pipe, wherein the alignment mechanisms are configured for selectably adjusting an orientation of the wheels to allow the robotic apparatus to move along a straight path or a helical path on the pipe.

In various embodiments, at least one of the wheels may have a concave shaped surface for engaging the pipe. At least one of the wheel assemblies, in various embodiments, may include a motor for rotating the wheel of the corresponding assembly. The motor, in an embodiment, may be situated inside of the wheel of the corresponding assembly.

The clamping mechanism, in various embodiments, may include one or more biasing members for generating the pulling force. The one or more biasing members, in some embodiments, may be configured to passively generate the pulling force and may, in an embodiment, include at least one of a tension spring, a compression spring, and a torsion spring. The one or more biasing members, in some embodiments, may be configured to actively generate the pulling force.

The clamping mechanism, in various embodiments, may include a first arm member connecting the first wheel assembly with the second wheel assembly; a second arm member connecting the first wheel assembly with the third wheel assembly; and one or more biasing members for applying a pulling force to engage the wheels on opposing sides of the pipe, the one or more biasing members either connecting the first arm member to the second arm member or connecting the first wheel assembly to the first arm member and to the second arm member. The clamping mechanism, in an embodiment, may further include a third arm member and a fourth arm member arranged parallel and adjacent to the first arm member and the second arm member, respectively, thereby forming first and second parallelogram-shaped linkages between the first wheel assembly and the second wheel assembly and between the first wheel assembly and the third wheel assembly, respectively, wherein the parallelogram-shaped linkages maintain the wheel assemblies in parallel alignment with one another regardless of a relative position of the wheel assemblies to one another.

The clamping mechanism, in various embodiments, may be offset from and parallel to a plane shared by the wheels. The robotic device, in various embodiments, may include an open side situated opposite the clamping mechanism, through which an obstacle extending from the pipe may pass unobstructed. The robotic apparatus, in various embodiments, may further include one or more members configured to extend across the open side of the robotic apparatus to prevent the robotic apparatus from falling off the pipe. The one or more members, in some embodiments, may be configured to pivot along a plane of the open side to accommodate passage of an obstacle through the open side of the robotic apparatus.

The alignment mechanism, in various embodiments, may be configured to adjust the orientation of a corresponding wheel in a rotational direction relative to an axis that is normal to the pipe. Adjusting the orientation of the wheels, in an embodiment, may cause the robotic apparatus to move along a helical path along the pipe. The alignment mechanism, in various embodiments, may include a wheel frame to which the wheel is rotatably coupled about a first axis; a base plate to which the wheel frame is rotatably coupled about a second axis orthogonal to the first axis; and a motor configured to rotate the wheel frame about the second axis, thereby adjusting the orientation of the wheel relative to the base plate.

The robotic apparatus, in various embodiments, may further include a sensor assembly for inspecting the pipe or an environment surrounding the pipe. The sensor assembly, in some embodiments, may include a sensor, an arm member rotatably coupling the sensor to the robotic apparatus, and an actuator configured to rotate the arm member about the rotatable coupling to move the sensor towards or away from the pipe.

In another aspect, the present disclosure is directed to a method for navigating an obstacle on a pipe with a robotic apparatus. The method, in various embodiments may comprise the steps of providing a robotic apparatus comprising: (i) a first wheel configured for positioning on a first side of the pipe, (ii) a second wheel and a third wheel configured for positioning on a second, opposing side of the pipe, and (iii) a clamping mechanism connecting the first wheel to the second and third wheels, and situated offset from and parallel to a plane shared by the wheels so as to define an open side situated opposite the clamping mechanism; advancing the robotic apparatus along a helical pathway on the pipe to position the open side of the robotic apparatus in longitudinal alignment with the obstacle on the pipe; and advancing the robotic apparatus along a straight pathway on the pipe such that the obstacle passes unobstructed through the open side of the robotic apparatus.

Advancing the robotic apparatus along a helical pathway, in various embodiments, may include adjusting an orientation of at least one of the wheels rotationally relative to an axis that is normal to the pipe. Advancing the robotic apparatus along a straight pathway on the pipe, in various embodiments, may include adjusting an orientation of the wheels to be in alignment with a longitudinal axis of the pipe.

The robotic apparatus, in various embodiments, may include one or more members configured to extend across the open side of the robotic apparatus to prevent the robotic apparatus from falling off the pipe, wherein advancing the robotic apparatus along a straight pathway on the pipe such that the obstacle passes unobstructed through the open side of the robotic apparatus includes allowing the one or more members to pivot along a plane of the open side to accommodate passage of the obstacle through the open side of the robotic apparatus. The method, in various embodiments, may further include adjusting an orientation of two or more of the wheels in opposing directions to advance the robotic apparatus sideways relative to a longitudinal axis of the pipe and thereby reposition the robotic apparatus on the pipe to account for wheel slip.

BRIEF DESCRIPTION OF THE DRAWINGS

Illustrative, non-limiting example embodiments will be more clearly understood from the following detailed description taken in conjunction with the accompanying drawings.

FIG. 4A is a cutaway view of an internal motor within a wheel in accordance with an embodiment of the present disclosure;

FIG. 4B is a perspective view of a wheel assembly in accordance with an embodiment of the present disclosure;

FIG. 5A, FIG. 5B, and FIG. 5C depict various views of a robotic apparatus attached to a pipe in accordance with an embodiment of the present disclosure;

FIG. 9A, FIG. 9B, FIG. 9C, FIG. 9D, FIG. 9E, FIG. 9F, FIG. 9G, FIG. 9H illustrate the robotic apparatus passing an obstacle in accordance with an embodiment of the present disclosure;

DETAILED DESCRIPTION

Figure 1B:
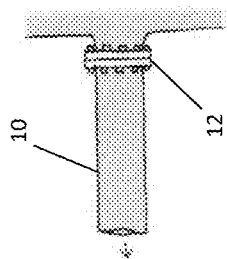
FIG. 1A, FIG. 1B, FIG. 1C, FIG. 1D, and FIG. 1E illustrate various obstacles that may be found along a piping system.
Figure 1D:
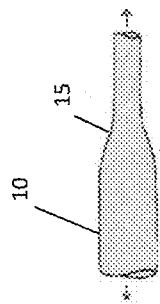
Figure 1E:
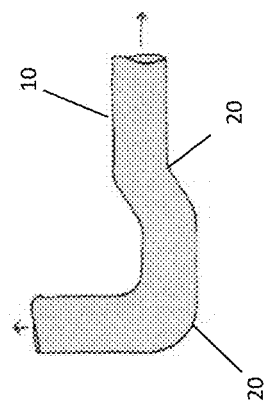
Figure 1A:
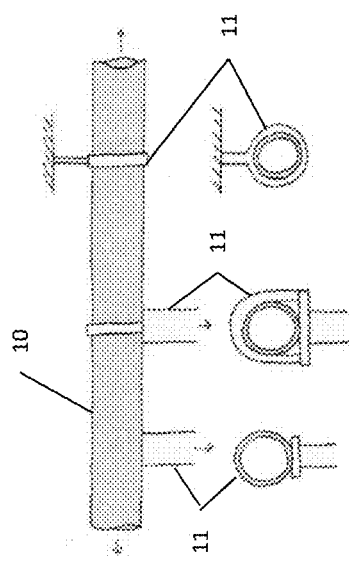
Figure 1C:
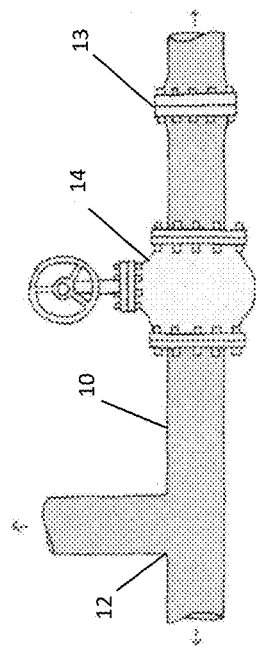

Embodiments of the present disclosure are directed to a robotic apparatus for traversing the exterior of piping systems, such as ones commonly found in chemical plants, power plants, manufacturing plants, and infrastructure. Piping systems can be complex and present various obstacles that can make it difficult to traverse individual pipes in an efficient and effective manner. For example, as shown in FIG. 1A, FIG. 1B, FIG. 1C, FIG. 1D, and FIG. 1E, representative obstacles may include supports 11 (FIG. 1A), junctions 12 (FIG. 1B and FIG. 1C), flanges 13 (FIG. 1C), valves 14 (FIG. 1C), vents or bleeders (similar to smaller valves), changes in diameter 15 (FIG. 1D), and bends 16 (FIG. 1E), amongst others. Various embodiments of the robotic apparatus may be configured to traverse pipes 10 and navigate such obstacles as encountered through a unique architecture and approach, as later described in more detail.

Embodiments of the present disclosure are directed to a robotic apparatus that may also traverse the exterior of other structures that are similarly shaped, such as structural cables (e.g. on suspension bridges), structural beams, powerlines, underwater cables and underwater piping systems.

Embodiments of the present disclosure may be useful in many applications including, without limitation:
- Pipeline inspection using cameras, non-destructive testing (NDT or NDI), or other sensors;
- Inspecting equipment in the vicinity of the piping system
- Performing maintenance on the piping system (e.g., cleaning the external surface, removing insulation, applying a patch/clamp to stop a leak)
- Transporting tools or equipment along the piping system (e.g., facilitating installation of sensors on the pipe).

Various embodiments of the robotic apparatus may be capable of traversing pipes arranged in any orientation (including horizontal and vertical), and pipes made of any material (e.g., steel, aluminum), even those with insulation about the exterior of the pipe. Insulation is typically a semi-rigid material, such as a mineral wool or calcium silicate, protected by a thin metal jacket, such as aluminum or stainless steel.

Generally speaking, embodiments of the robotic apparatus of the present disclosure may attach to a pipe by applying a clamping force on opposing sides of the pipe. Various embodiments may be capable of holding a static position on the pipe and may support its own weight on a range of pipe sizes in any orientation (e.g., horizontal or vertical). The robotic apparatus, in various embodiments, may be configured to drive along a path in the longitudinal direction of the pipe, as well as along a helical path (i.e., circumferential and longitudinal), on pipes of varying sizes and orientation. Such maneuvering, in combination with the ability to expand or contract the clamping mechanism around the pipe, and an open-sided architecture, may allow the robotic apparatus to navigate a variety of bends and obstacles encountered along the length of the pipe. A low profile of the robotic apparatus may enable it to drive along pipes in close proximity to other pipes or obstacles situated close by, and an optional fail-safe mechanism may be included to prevent the robotic apparatus from falling to the ground in the event its wheels decoupled from the pipe. The robotic apparatus may additionally be capable of actively sensing and controlling the amount of clamping force it exerts on the pipe, thereby minimizing the risk that its wheels slip along the pipe while ensuring that the robotic apparatus does not damage the pipe or insulation. Further, the robotic apparatus may be capable of actively sensing whether the wheels slip on the pipe surface and actively control individual wheels to steer the robotic apparatus back to the centerline of the pipe.

In various embodiments, the robotic apparatus may be configured to carry and deploy a payload along the pipe, such as cameras (e.g. visual spectrum and IR cameras), various sensors like NDT sensors (e.g., ultrasonic testing probes, pulsed eddy current probes, digital radiography equipment, acoustic sensors) and lower explosive limit (LEL) sensors for the purpose of inspecting the piping system or equipment in its vicinity, and/or other payloads like tools and equipment. The robotic apparatus, in various embodiments, may include an onboard power supply (e.g., batteries) and operate via wireless communication with an operator, thereby obviating the need for a power cord or tether.

High-Level Architecture

Figure 2:
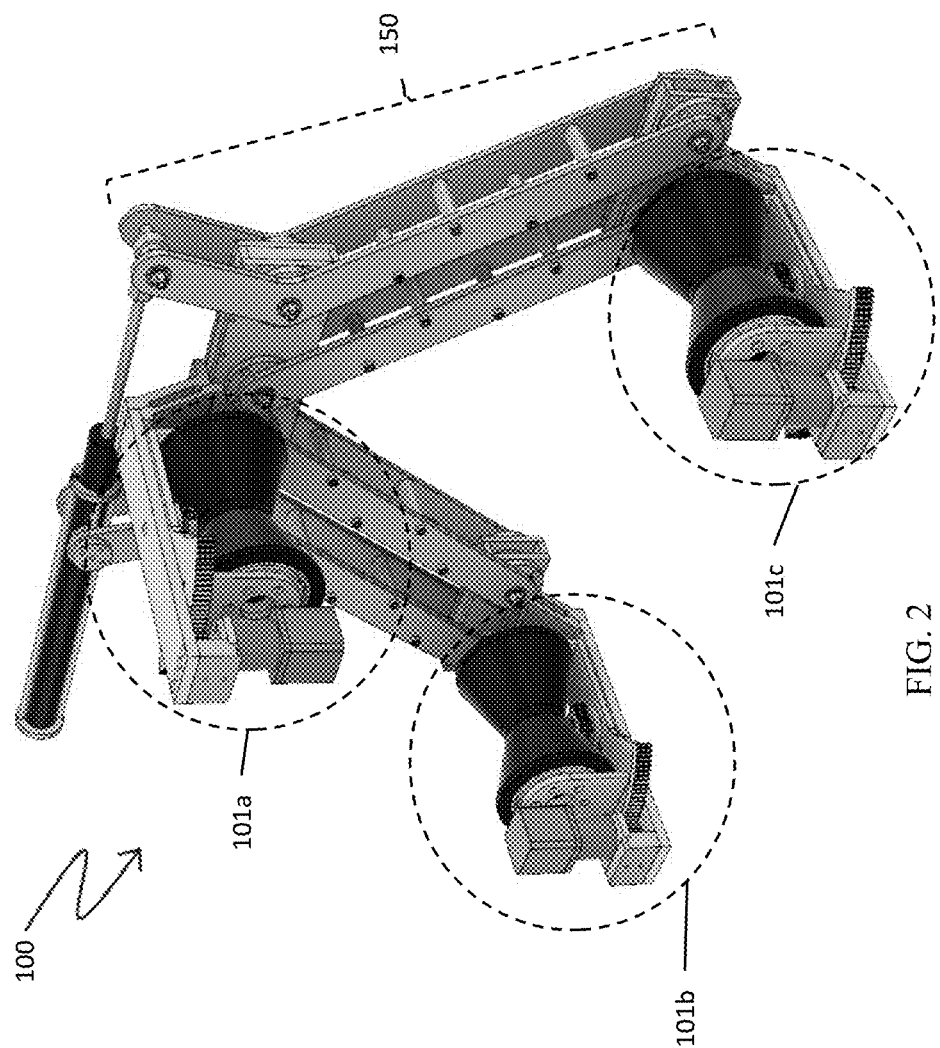
FIG. 2 is a perspective view of a robotic apparatus in accordance with an embodiment of the present disclosure.

Referring now to FIG. 2, robotic apparatus 100 of the present disclosure may generally include two or more wheel assemblies 101 configured for positioning on opposing sides of pipe 10, and a clamping mechanism 150 for adjusting the distance between the two or more wheel assemblies to secure robotic apparatus 100 to pipe 10. One or more wheels of the two or more wheel assemblies 101 may be powered such that robotic apparatus may traverse along pipe 10 in a longitudinal direction. The wheels, in various embodiments, may be reoriented to allow robotic apparatus 100 to move along a helical path on pipe 10, and thereby position robotic apparatus 100 to pass over a particular portion(s) of pipe 10 and/or avoid an obstacle(s) extending from a surface of pipe 10, as later described in more detail.

FIG. 3A, FIG. 3B, FIG. 3C, and FIG. 3D depict several views of a representative embodiment of robotic apparatus 100. The representative embodiment shown includes three wheel assemblies 101a, 101b, 101c arranged in a triangular configuration in a common plane ("wheel engagement plane" 104), such that wheel assembly 101a is positioned for engaging a first side of pipe 10, and wheel assemblies 101b, 101c are positioned for engaging a second, opposing side of pipe 10. Clamping mechanism 150 is offset from the wheel engagement plane 104 and couples wheel assemblies 101a, 101b, 101c. As configured, wheel assemblies 101a, 101b, 101c may traverse along an outer portion of pipe 10, while the offset positioning of clamping mechanism 150 allows clamping mechanism 150 to travel through the air or water alongside pipe 10. The present configuration provides robotic apparatus 100 with an open side 102 (as best seen in FIG. 5C), situated opposite clamping mechanism 150, through which an obstacle extending from the outer surface of pipe 10 may pass unobstructed, thereby allowing robotic apparatus to traverse such obstacles on pipe 10 as later described in more detail.

Wheel Assembly 101

Still referring to FIG. 3A, FIG. 3B, FIG. 3C, and FIG. 3D, each wheel assembly 101 may generally include a wheel 110 and an alignment mechanism 120. Generally speaking, wheel 110 may be configured to engage and rotate along an outer surface of pipe 10, and alignment mechanism 120 may be configured to adjust an orientation of wheel 110 and thereby define a path to be followed by robotic apparatus as it traverses pipe 10.

Wheel 110, in various embodiments, may include any rotatable body suitable for engaging and rotating along an outer surface of pipe 10. To that end, wheel 110 may generally include a rotating body with a contact surface 112, and may be rotatably coupled with a wheel frame 114.

Wheel 110 may be of any shape and construction suitable for the aforementioned purpose such as, without limitation, disc- or cylindrical-shaped. While standard wheels may be utilized, in various embodiments, it may be advantageous for wheel 110 to have a shape specifically designed to accommodate, and thereby more effectively engage, the rounded shape of the outer surface of pipe 10. To that end, in various embodiments, contact surface 112 may be substantially inverted (e.g., v-shaped, hourglass shaped), with contact surface 112 having a concave curvature dimensioned to conform to the rounded shape of pipe 10. As best shown in FIG. 5C, the hourglass shape of contact surface 112 may serve to maximize the contact area between wheel 110 and pipe 10 compared with a standard cylindrical wheel with a flat or convex contact surface, as the hourglass shaped contact surface 112 of the present disclosure essentially wraps around the curvature of pipe 10, providing contact with not just the center of the pipe, but also with the top quarters as well. By enhancing overall contact area between wheel 110 and pipe 10, more friction is available to securely couple robotic apparatus 100 to pipe 10. By distributing the contact area between wheel 110 and pipe 10 around the circumference of the pipe, wheel 110 has a favorable lever arm to support off-axis forces, such as the typical force from the clamping mechanism. Thus, the wheel's shape allows robotic apparatus 100 to maintain a given circumferential orientation on pipe 10 (e.g., upright, canted diagonally) without slipping upside-down on pipe 10.

Further, the hourglass shape of contact surface 112, in various embodiments, may act to automatically center wheel 110 along a longitudinal centerline of pipe 10, as shown in FIG. 5C. As configured, wheel 110 may be less likely to disengage from pipe 10 entirely, as contact between the inwardly sloping contact surface 112 and the rounded surface of pipe 10 may bias wheel 110 to center itself over the longitudinal centerline of pipe 10. This may be particularly beneficial in embodiments in which wheel assemblies 101 are arranged within a common engagement plane 104, as shown, since such a configuration generally clamps on pipe 10 from two radial directions instead of three or more radial directions were wheel assemblies 101 to be positioned in more than two circumferential positions about pipe 10. Still further, contact surface 112 may be shaped and dimensioned such that it functions effectively on a range of pipe sizes. The straight edges of the wheel profile, as seen from a direction normal to the concentric axis of the wheel, may be purposefully chosen so that the angular distance between the contact points with respect to the center of the pipe is constant for any pipe size. However, the linear distance between the contact points increases with the pipe size in a manner such that the range of pipe sizes on which wheel 110 is effective is limited by the total width of wheel 110.

The shape of contact surface 112 may be especially suitable for helical motion around a pipe, including the helical motion that robotic apparatus 100 may exhibit. Consider the plane that includes the central axis of the wheel and a vector that is normal to the surface of the pipe. When the wheel is oriented to drive straight along the longitudinal axis of the pipe the cross-section of the pipe in the aforementioned plane is a circle. When the wheel is oriented to drive at an angle with respect to the longitudinal axis of the pipe the cross-section of the pipe in the aforementioned plane is an ellipse. This effectively changes the curvature of the section of the pipe that the wheel is driving on, similar to how a change in pipe size changes the pipe's curvature. Similar to how the wheel can adapt to a range of pipe sizes, it can also adapt to a range of turning angles that effectively change the curvature of the pipe under the wheel. In general, the contact area between the wheel and the pipe increases as the curvature decreases. Hence, the contact area increases as the pipe size increases and as the angle between the wheel's direction of travel and the longitudinal axis of the pipe increases.

Alignment mechanism 120, in various embodiments, may include any mechanism suitable for adjusting an orientation of wheel 110, and thereby define a path to be followed by robotic apparatus as it traverses pipe 10. In particular, alignment mechanism 120, in various embodiments, may be configured to adjust the orientation of an associated wheel 110 rotationally, with respect to an axis that is normal to pipe 10, to steer robotic apparatus along pipe 10. That is, alignment mechanism 120, in various embodiments, may adjust the orientation of an associated wheel 110 about a yaw axis 103 of robotic apparatus 100 (shown in FIG. 3C, FIG. 5C, FIG. 8A, FIG. 8B, FIG. 8C, FIG. 8D, FIG. 8E, and FIG. 8F) such that wheel 110 is reoriented clockwise or counterclockwise about an axis extending normal to the underlying surface of pipe 10. As configured, alignment mechanism 120 may adjust wheel 110 orientation to traverse pipe 10 along a straight pathway (i.e., wheel 110 orientation aligned with yaw axis 103 of robotic apparatus 100 and longitudinal axis of pipe 10) or along a helical pathway (i.e., yawed wheel 110 orientation, adjusted clockwise or counterclockwise relative to an axis extending normal to the underlying surface of pipe 10).

Referring to FIG. 4B, in an embodiment, alignment mechanism 120 may include a motor 122 and a base plate 124 to which wheel frame 114 may be rotatably coupled. Motor 122 may engage wheel frame 114 to rotate wheel frame relative to base plate 124, and thereby adjust an orientation of wheel 110 relative to base plate 124. In the embodiment shown, base plate 124 may be fixedly coupled to clamping mechanism 150, and wheel 110 may be reoriented relative to robotic apparatus as a whole. To facilitate engagement between motor 122 and wheel frame 114, each may be provided with gear teeth 123, 116, respectively, which may be interfaced with one another such that rotation of motor 122 causes rotation of wheel frame 114 about an axis normal to base plate 124. Of course, this is merely an illustrative embodiment of a suitable mechanism for adjusting an orientation of wheels 110 of robotic apparatus 100, and one of ordinary skill in the art will recognize other suitable alignment mechanisms within the scope of the present disclosure.

In certain scenarios, one or more alignment mechanisms 120 may be configured to individually adjust the respective orientations of wheels 110 by different amounts and/or in different directions. When all wheels 110 are turned by the same amount in the same clockwise or counter-clockwise direction, robotic apparatus 100 may travel along a helical pathway. In contrast, when wheels 110 are oriented in opposite directions, such that the wheels 110 on one side of pipe 10 turn in one direction (e.g. clockwise) and the wheels on the opposite side of pipe 10 turn in the opposite direction (e.g. counter-clockwise), robotic apparatus 100 may travel along a different pathway. In the latter case, wheels 110 may travel such that robotic apparatus 100 moves along the longitudinal axis of pipe 10 and translates sideways with respect to the same axis. This may be beneficial if wheels 110 slip, for example due to the weight of robotic apparatus 100, away from the centerline of pipe 10. This method for self-adjusting the position of robotic apparatus 100 on the pipe is later illustrated in FIG. 15A, FIG. 15B, FIG. 15C, and FIG. 15D.

According to exemplary embodiments of the present disclosure, the angular orientation of the wheels may "lock" once axial movement of robotic apparatus 100 on pipe 10 commences. In this way, the desired travel pattern, e.g., helical travel with a 5° off-axis alignment of wheels 110, may be maintained as robotic apparatus 100 moves along pipe 10. Various locking features may be employed to detachably secure wheel frame 114 (and thus wheel 110) in the desired angular orientation, as will be apparent to persons skilled in the art.

Wheel assembly 101, in various embodiments, may further include a motor 130 for driving rotation of wheel 110. Motor 130 may include any motor such as, without limitation, a brushed DC motor or the like, suitable for driving rotation of an associated wheel 110 of wheel assembly 101.

Figure 3A:
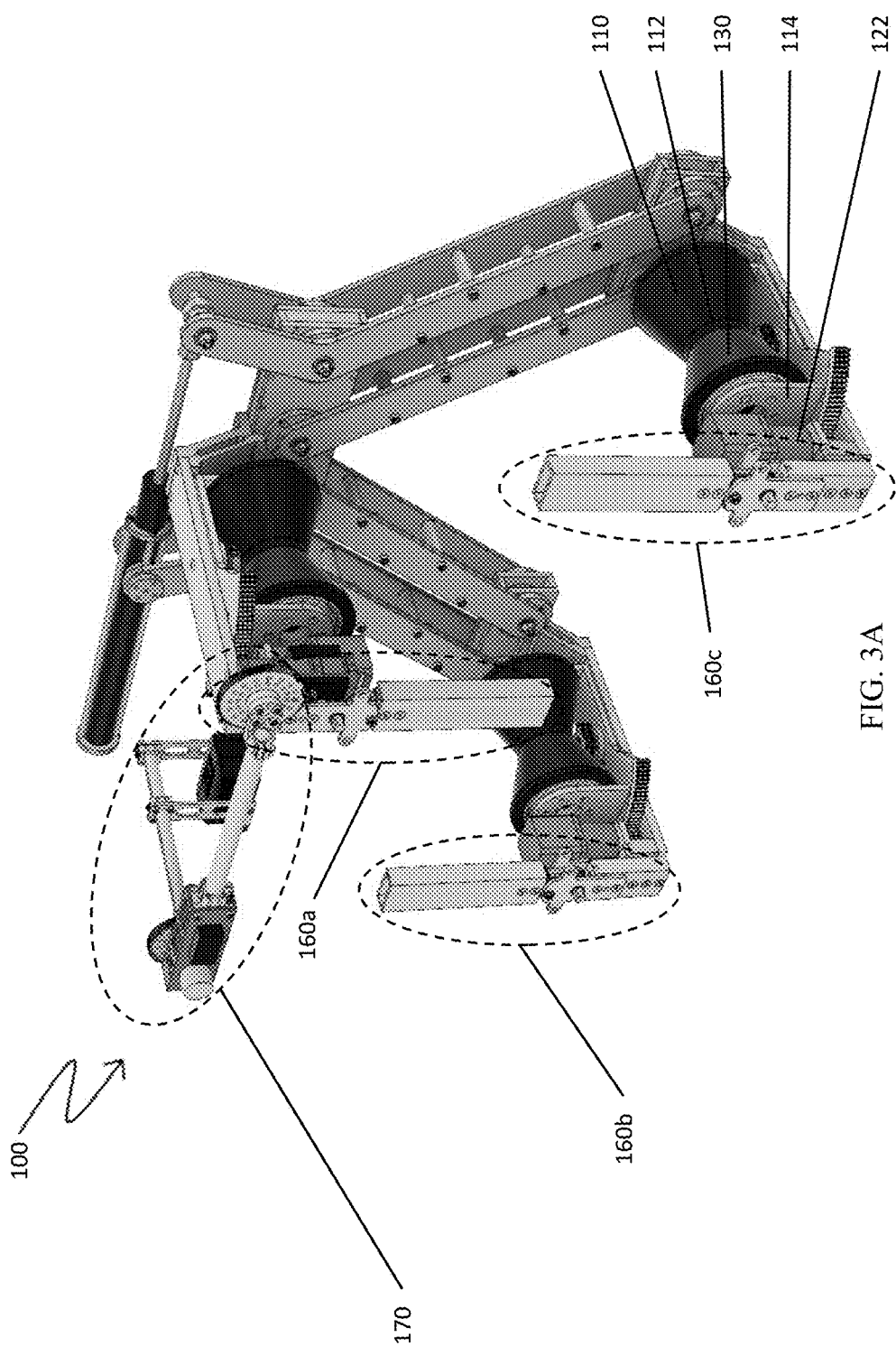
FIG. 3A, FIG. 3B, FIG. 3C, and FIG. 3D depict various views of a robotic apparatus in accordance with an embodiment of the present disclosure.
Figure 3B:
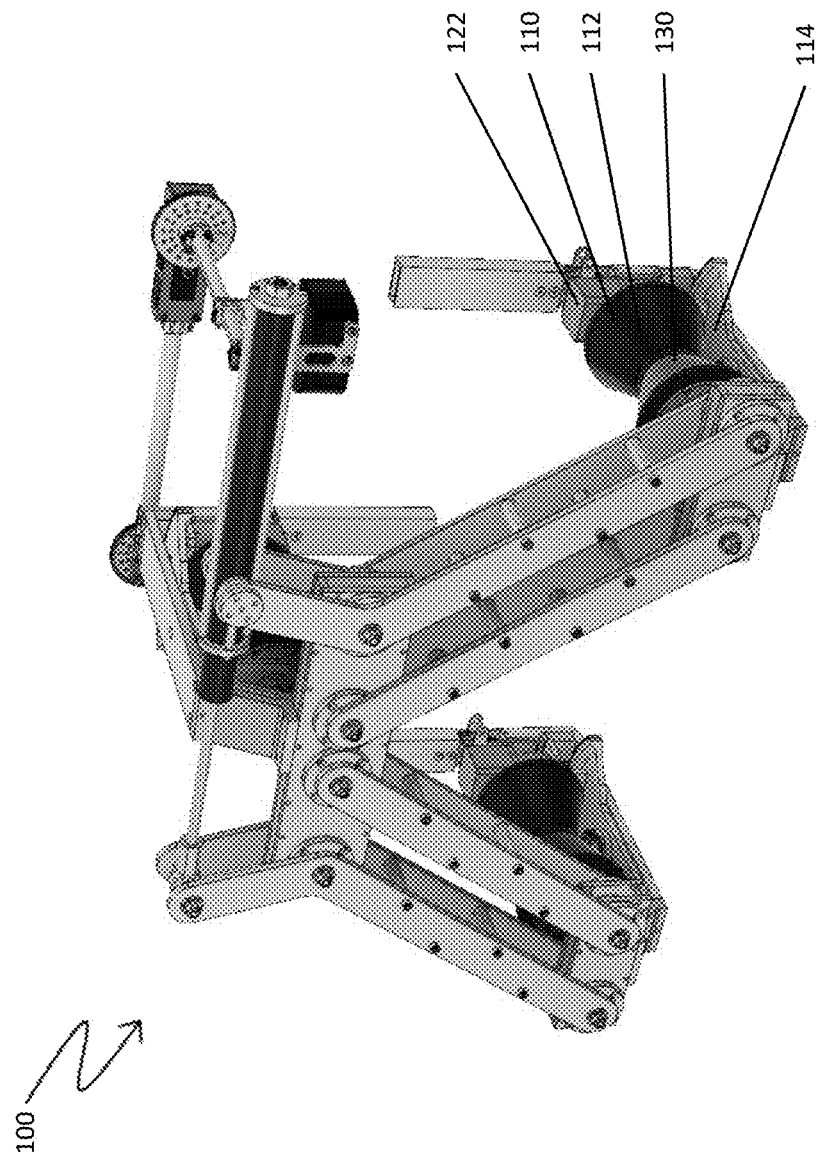
Figure 3C:
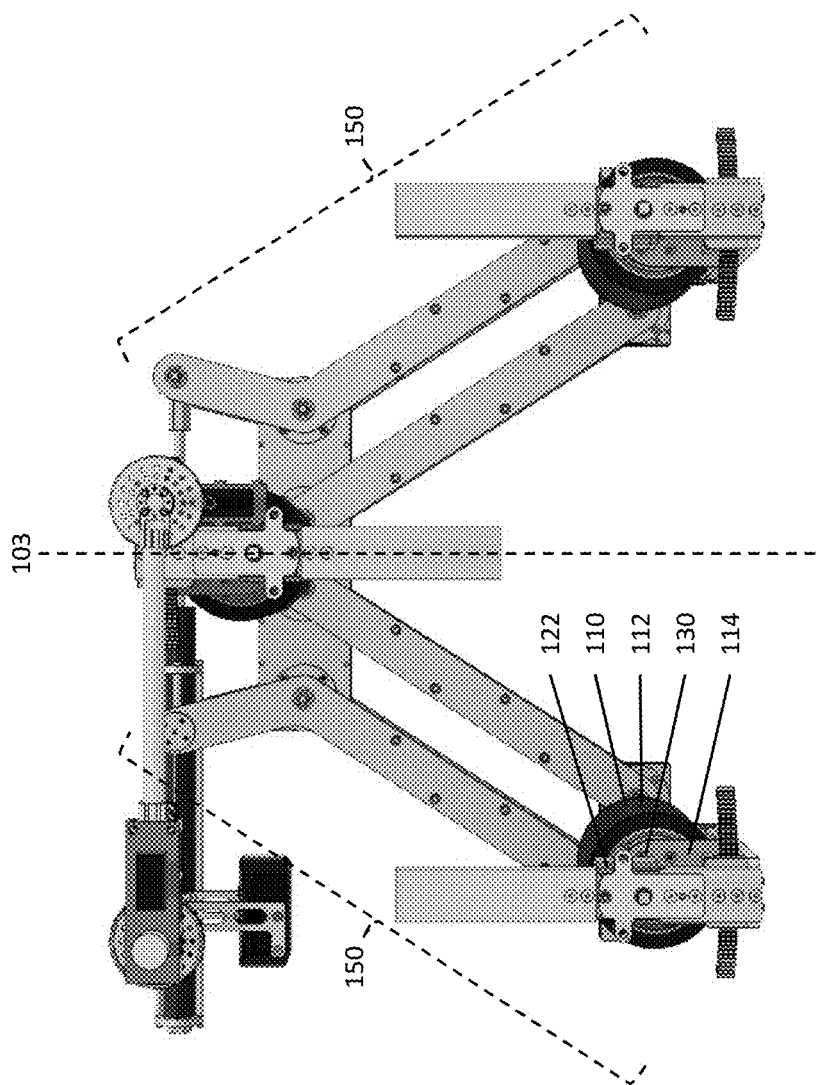
Figure 3D:
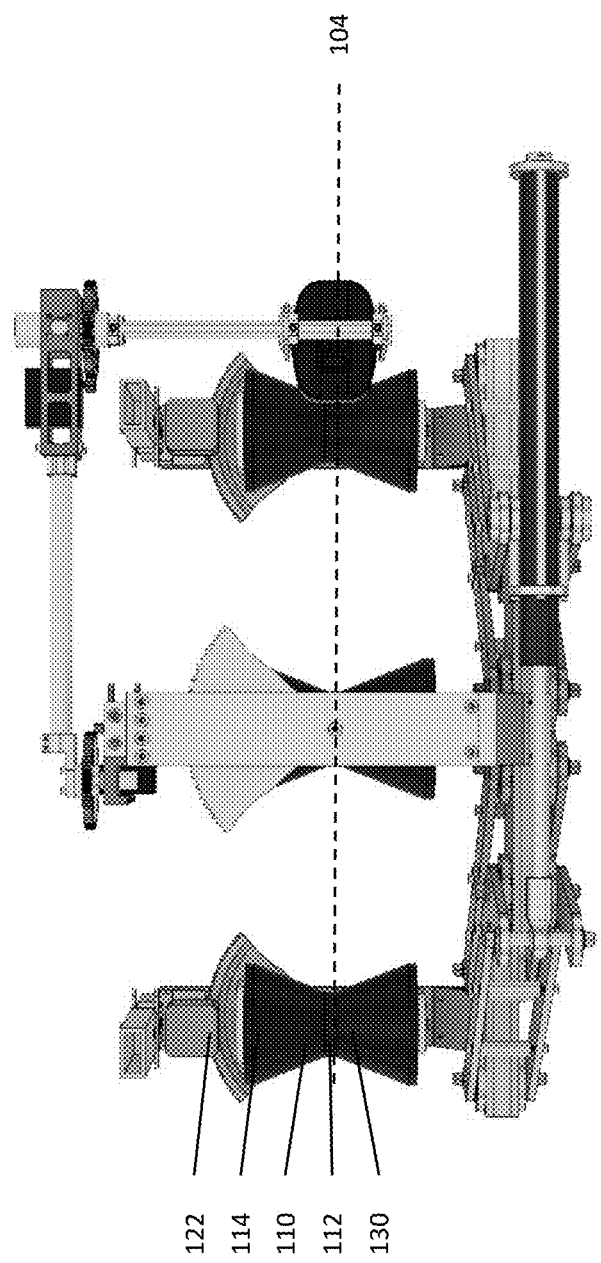

As shown in FIG. 3A, FIG. 3B, and FIG. 3C, in various embodiments, motor 130 may be positioned external to wheel 110 and connected thereto via a traditional drive train for rotating wheel 110. Motor 130, in other embodiments, may instead be packaged within wheel 110, as shown in FIG. 4A and FIG. 4B. In particular, motor 130 may be placed inside wheel 110 with its output shaft 132 concentric to the rotation axis 131 of wheel 110, as shown. Motor 130 may be rigidly mounted to a cylindrical housing 134, which is designed to attach to wheel frame 114. As configured, cylindrical housing 134 may act as a shaft that supports wheel 110 through a set of bearings (e.g. tapered roller bearings) 136 while allowing wheel 110 to rotate with respect to cylindrical housing 134. Output shaft 132 of motor 130 may be coupled to wheel 110, as shown, so that motor 130 can control the rotation of wheel 110. Output shaft 132 of motor 130, in various embodiments, may also be favorably supported by wheel frame 114 through an additional bearing (e.g. roller bearing) 138.

Wheel assembly 101 may further include one or more controllers (not shown) for controlling operation of motor(s) 130, such as rotational speed, torque, and the like. The controllers may receive commands from various locations. For example, one of the controllers mounted with respect to robotic apparatus 100 may function as a "master" controller, and the other controllers may function as "slave" controllers, such that the slave controllers respond to commands received from the master controller. Alternatively, each of the controllers may operate independently and may receive independent commands. The commands may be remotely transmitted, e.g., by wireless (or wired) communication, as is known in the art. The commands may also be pre-programmed, in whole or in part, in the controller(s), e.g., time-based commands to operate according to clock-based criteria.

Although exemplary robotic apparatus 100 is depicted with three motors 130, the disclosed apparatus may be implemented such that a motor is provided for less than all wheels associated with the apparatus. For example, a single drive motor 130 associated with a single wheel 110 may be provided, and the other wheels 110 may rotate in response to movement that is initiated by the single motor 130 (and associated wheel 110). Similarly, a pair of motors 130 may be provided for an apparatus that includes three wheels 110, such that two wheels 110 may receive drive force from associated motors 130, while the third wheel 110 rotates in response to movement of the apparatus relative to the pipe 10.

In exemplary embodiments of the present disclosure, the relative speed of the individual wheels 110 may be controlled so as to enhance the operation of the apparatus. For example, it may be desired to drive the center wheel (e.g., that of wheel assembly 101a) faster than either of the outer wheels (e.g., those of wheel assemblies 101b, 101c) when navigating a turn or bend in the pipe 10. In such circumstance, the controllers may be programmed to increase the drive force to the center wheel 110 and/or reduce the drive force to outer wheel(s) 110. Alternatively, it may be desirable to drive the outer wheels 110 faster than the center wheel 110 when navigating a turn or bend in the pipe 10. In such circumstance, the controllers may be programmed to increase the drive force to the outer wheel(s) 110 and/or reduce the drive force to the center wheel 110. The noted adjustments may be initiated manually, e.g., by an operator, or may be initiated automatically, e.g., based on sensing mechanism(s) associated with the assembly that identify a turn/bend in the pipe 10 (e.g., based on sensing of the angular orientation of one or more aspects of the apparatus).

Clamping Mechanism 150

Figure 5B:
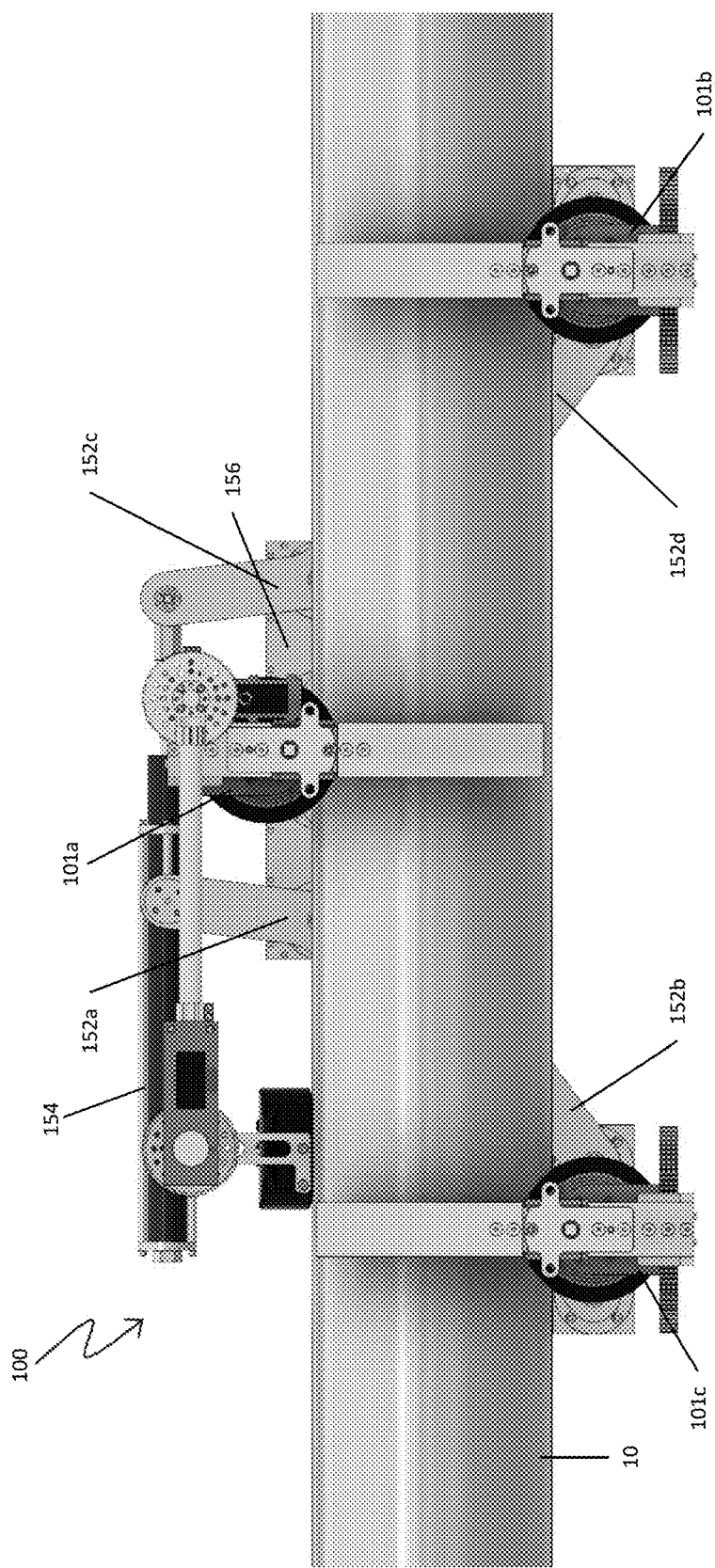
Figure 5C:
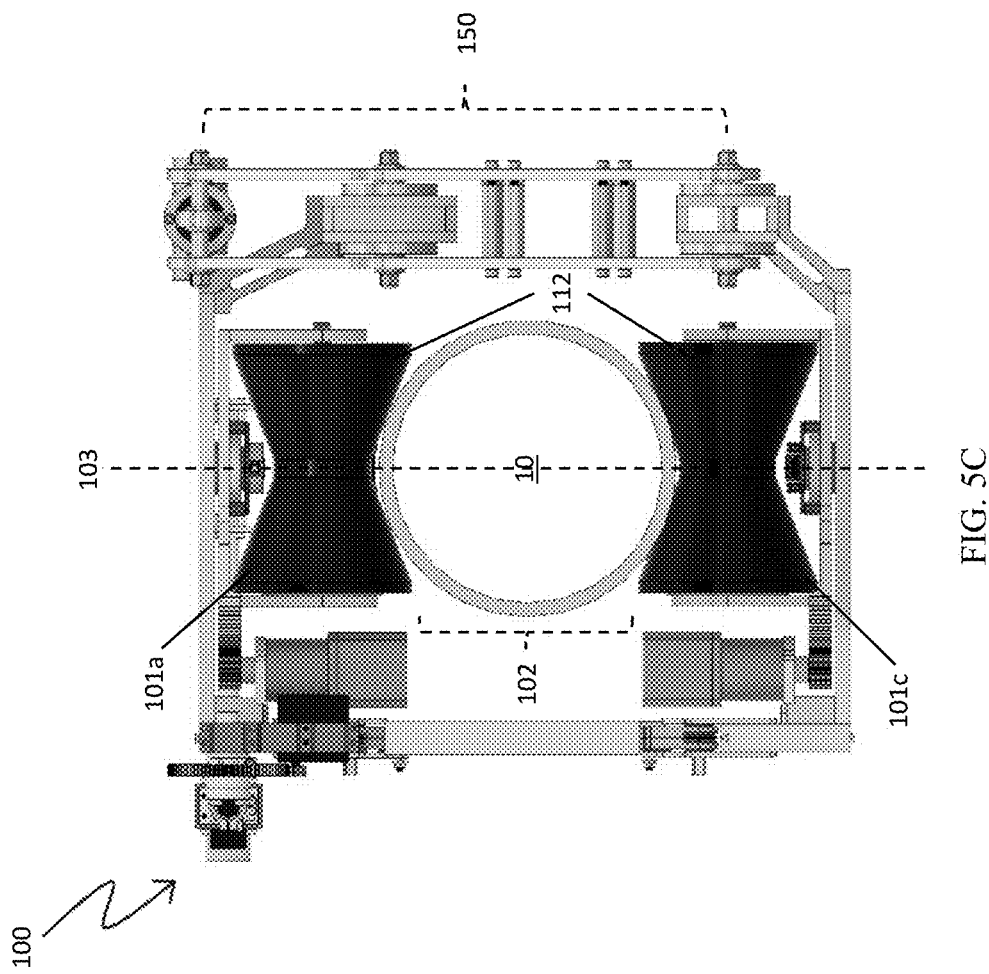

Referring ahead to FIG. 5A, FIG. 5B, and FIG. 5C, clamping mechanism 150 of robotic apparatus 100, in various embodiments, may generally include one or more arm members 152 and one or more biasing members 154. Arm member(s) 152, in various embodiments, may connect wheel assemblies 101 on opposing sides of pipe, and biasing member(s) 154 may apply a pulling or pushing force on arm members 152 that causes the wheel assemblies to engage the opposing sides of pipe 10, thereby securing robotic apparatus 100 to pipe 10 as later described in more detail.

Arm members 152, in various embodiments, may be arranged in pairs, with the members of a given pair arranged parallel to one another and separated by a gap, as shown in FIG. 5A. The ends of each member 152 in a given pair may be rotatably coupled with the associated wheel assemblies 101 such that the given pair forms a parallelogram-shaped linkage between the corresponding wheel assemblies 101. The parallelogram-shaped linkage, in an embodiment, may act to keep the connected wheel assemblies 101 in parallel alignment with one another on either side of pipe 10 regardless of the relative positions of the connected wheel assemblies 101 (which may change with pipe diameter, as later described). By keeping the connected wheel assemblies 101 in parallel alignment with one another on opposing sides of pipe 10, the associated wheels 110 may more effectively engage the surface of pipe 10 and securely couple robotic apparatus 100 thereto. Additionally, keeping the connected wheel assemblies 101 in parallel alignment with one another is important for the alignment mechanism 120 to function properly. That is, yaw axis 103 about which alignment mechanism 120 turns wheel 110 should be normal to the surface of pipe 10.

For example, in FIG. 5A, arm members 152a, 152b form a pair with the aforementioned arrangement, and connect wheel assembly 101a with wheel assembly 101b. As configured, wheel assembly 101b may pivot clockwise (e.g., up and to the left) relative to wheel assembly 101a to engage a narrow diameter pipe 10, or may pivot counterclockwise (e.g., down and to the right) relative to wheel assembly 101a to engage a larger diameter pipe, and vice versa. As wheel assemblies 101a, 101b pivot relative to one another, the parallelogram-shaped linkage formed by arm members 152a, 152b causes the connected wheel assemblies 101a, 101b to remain in parallel alignment with one another on either side of pipe 10, thereby ensuring that wheel 110 of each remains flush and engaged with pipe 10. Similarly, arm members 152c, 152d form a pair with the aforementioned arrangement, and connect wheel assembly 101a with wheel assembly 101c. As configured, wheel assembly 101c may pivot counterclockwise (e.g., up and to the right) relative to wheel assembly 101a to engage a narrow diameter pipe 10, or may pivot clockwise (e.g., down and to the left) relative to wheel assembly 101a to engage a larger diameter pipe, and vice versa. As wheel assemblies 101a, 101c pivot relative to one another, the parallelogram-shaped linkage formed by arm members 152b, 152c causes the connected wheel assemblies 101a, 101c to remain in parallel alignment with one another on either side of pipe 10, thereby ensuring that wheel 110 of each remains flush and engaged with pipe 10.

Of course, in various embodiments, a single arm member 152 (as opposed to the aforementioned pairs) may be used connect two wheel assemblies 101. In such embodiments (not shown), alternative approaches may be employed to maintain the connected wheel assemblies 101 in parallel alignment, if desired. For example, a single arm member 152 may be used with a pair of wires in the same plane as the aforementioned pairs. The wires may attach directly to wheel assemblies 101 on each side of arm member 152. While arm member 152 would provide the necessary structural integrity, the wires would engage when arm member 152 pivoted and (based on the same kinematics as the parallelogram-shaped linkage) keep the connected wheel assemblies 101 in parallel alignment with one another. It should be recognized that two wires may be be needed since wires typically only carry loads in tension, not compression.

Biasing members 154, in various embodiments, may be configured to apply a force for pulling opposing wheel assemblies 101 toward opposing sides of pipe 10 to secure robotic apparatus 100 to pipe 10. Biasing members 154 may include any mechanism suitable for this purpose such as, without limitation, a gas tension spring (shown in FIG. 5A, FIG. 5B, and FIG. 5C), tension springs (shown in FIG. 17), compression springs, torsion springs, or any combination thereof. Additionally or alternatively, biasing mechanisms 154 may include one or more active biasing members (as opposed to the immediately aforementioned passive biasing members) such as a motorized pulley system, motorized lead screw, or a pneumatic/hydraulic actuator, or the like.

Figure 6B:
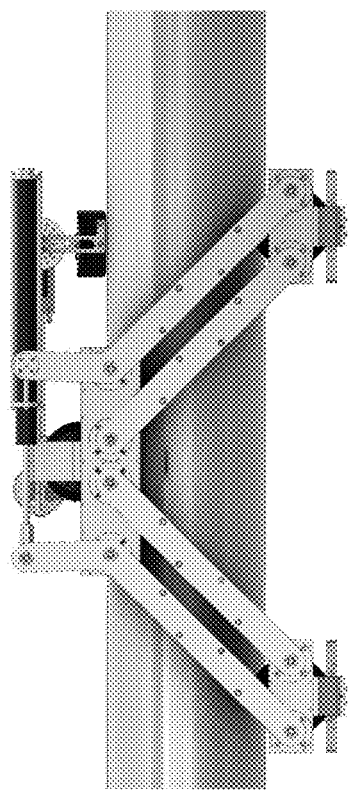
FIG. 6A and FIG. 6B depict a robotic apparatus on a smaller diameter pipe and a larger diameter pipe in accordance with an embodiment of the present disclosure.
Figure 6A:
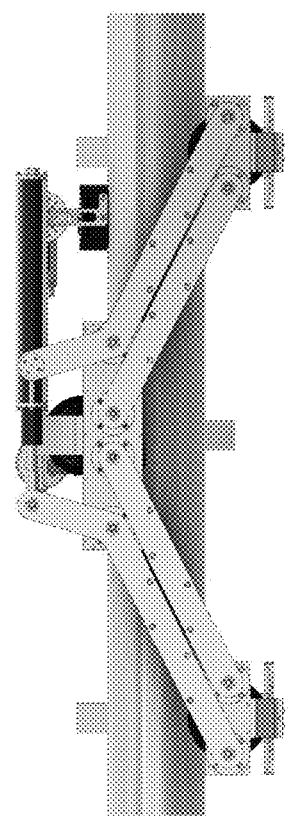
Figure 7:
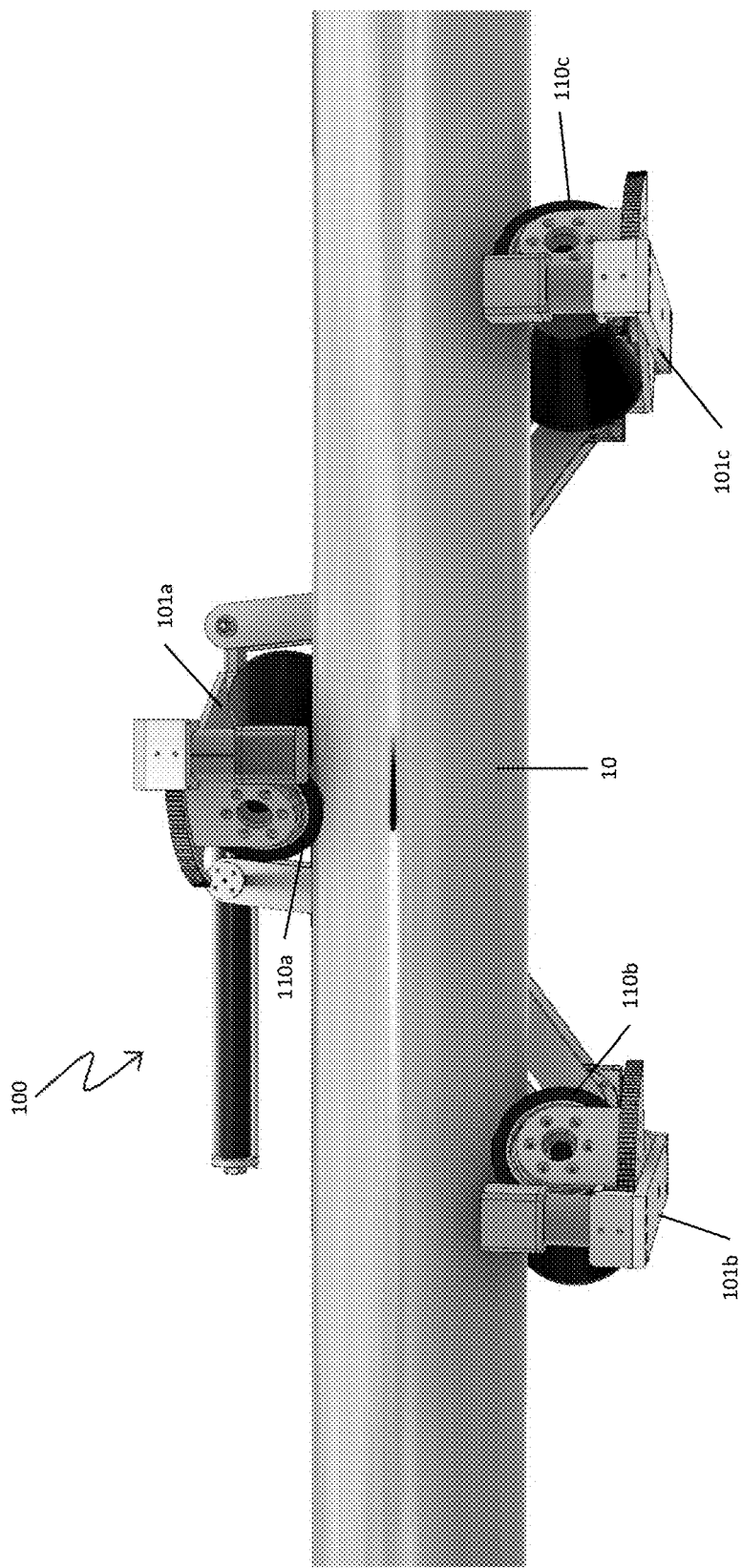
FIG. 7 illustrates a robotic apparatus with wheel alignment adjusted for helical travel along a pipe in accordance with an embodiment of the present disclosure.
Figure 8C:
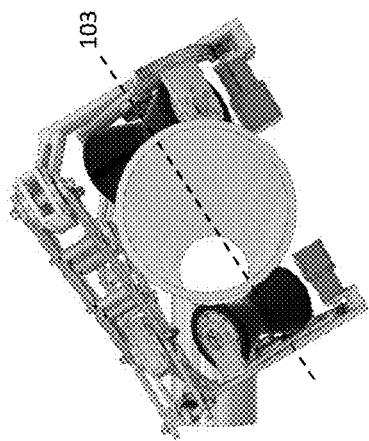
FIG. 8A, FIG. 8B, FIG. 8C, FIG. 8D, FIG. 8E, and FIG. 8F illustrate the robotic apparatus following a helical path to pass an obstacle in accordance with an embodiment of the present disclosure.
Figure 8F:
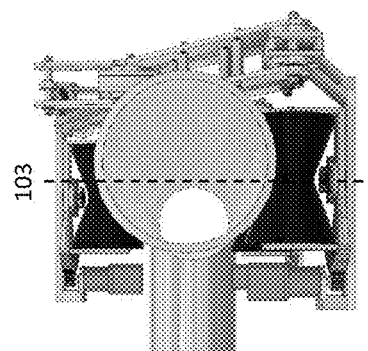
Figure 8B:
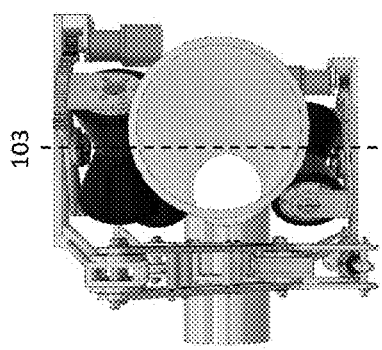
Figure 8E:
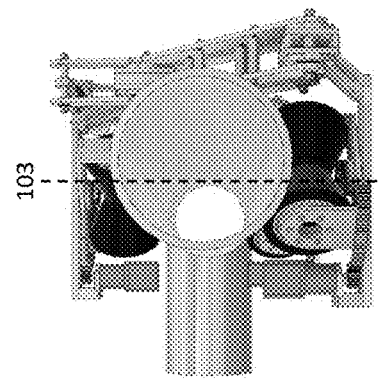
Figure 8A:
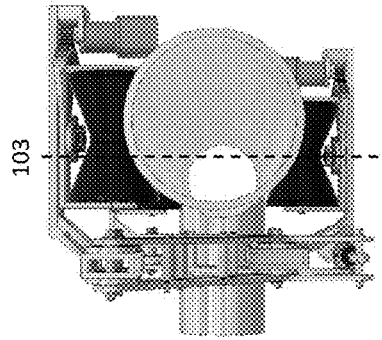
Figure 8D:
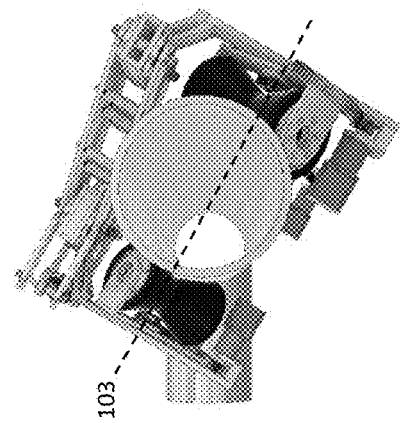

Clamping mechanism 150 as configured may automatically adjust the positions of wheel assemblies 101 relative to one another to accommodate pipes of varying diameters. For example, robotic apparatus 100 may compress significantly to accommodate small diameter pipes, resulting in a configuration in which wheel assemblies 101b, 101c are nearly coplanar with wheel assembly 101a along a longitudinal axis of pipe 10 (i.e., separated by the small diameter of pipe 10), but are situated far away from wheel assembly 101a along a longitudinal axis of pipe 10, as shown in FIG. 6A. Conversely, robotic apparatus 100 may expand significantly to accommodate large diameter pipes, resulting in a configuration in which wheel assemblies 101a, 101b, 101c are situated close to one another along a longitudinal axis of pipe 10, but wheel assembly 101a is situated far from wheel assemblies 101b, 101c (i.e., separated by the large diameter of pipe 10), as shown in FIG. 6B. Biasing members 154a, 154b, 154c, 154d, as configured, may continuously apply the pulling force between wheel assembly 101a and each of wheel assemblies 101b, 101c, thereby securely coupling (or "clamping") robotic apparatus 100 to pipe 10, regardless of its orientation about the circumference of pipe 10 and regardless of whether pipe 10 is oriented horizontally or vertically.

Referring back to FIG. 5A, FIG. 5B, and FIG. 5C, in a representative embodiment, biasing mechanism 154 may include a gas tension spring. As shown, the gas tension spring may couple the one or more arms 152 extending from wheel assemblies 101b, 101c to wheel assembly 101a. As the gas tension spring exerts a pulling force on the arm members 152 it creates a torque about the pivot points where the arm members 152 attach to the wheel assembly 101a. This torque will act to pull wheel assemblies 101b, 101c outwards and upwards relative to wheel assembly 101a, causing robotic apparatus 100 to compress onto pipe 10.

Figure 16:
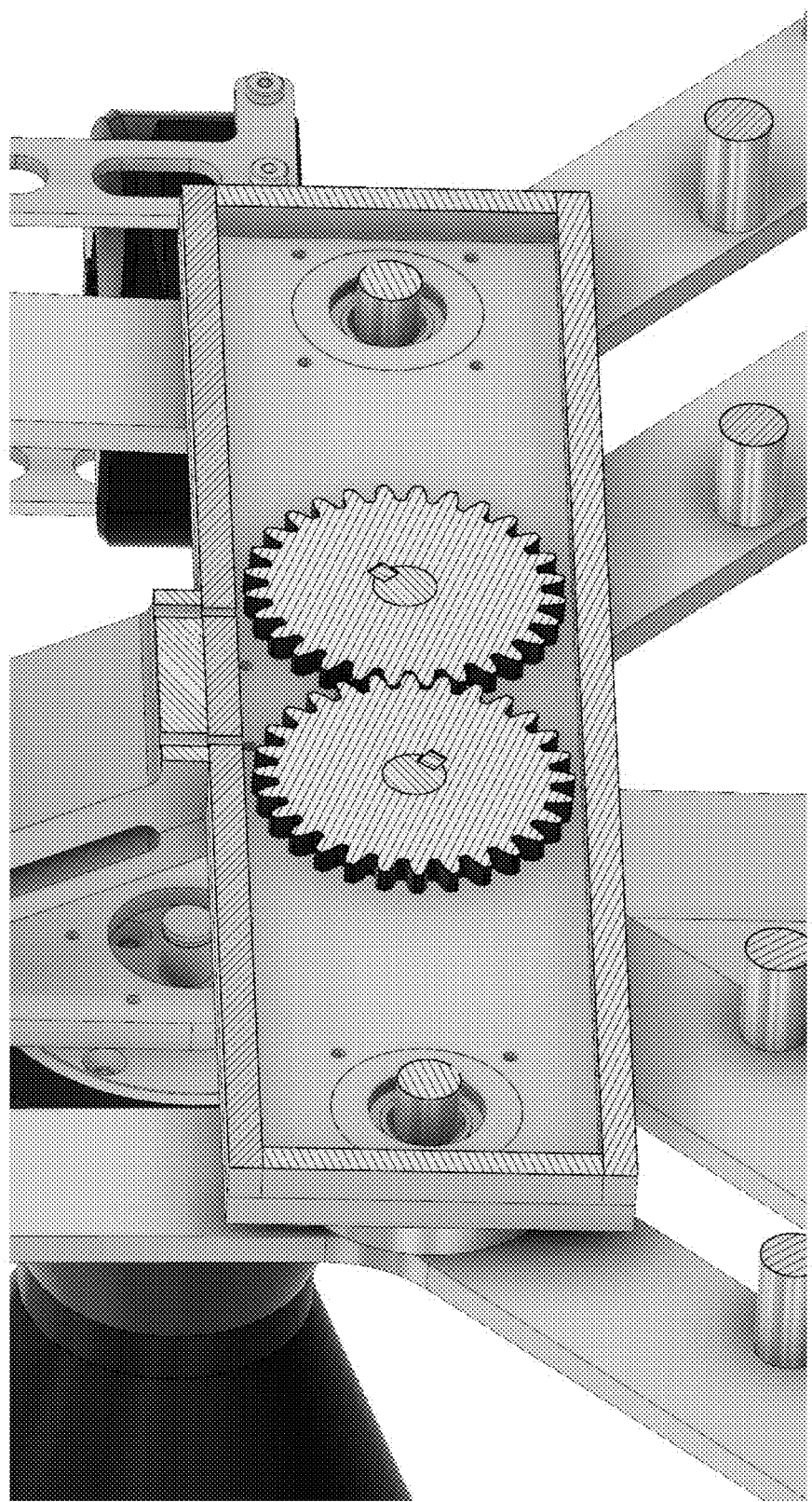
FIG. 16 is a cutaway view of gears of a clamping mechanism in accordance with an embodiment of the present disclosure.

Referring ahead to FIG. 16, in an embodiment, clamping mechanism 150 may include a set of gears that attach to the axles that connect the arm members 152b, 152d to the wheel assembly 101a. These gears are included to ensure that the arm members 152a, 152b, 152c, 152d pivot by the same angular displacement and the clamping mechanism 150 remains symmetrical with respect to wheel assembly 101a. The arm members 152 need to pivot by the same angular displacement so that the connected wheel assemblies 101 are not only in parallel alignment with respect to each other, but also with respect to pipe 10. In the alternative embodiment of FIG. 17 (later described), a specific mechanism is not needed to ensure that the member arms pivot equally. That is, if equal biasing members 154 connect the 101a wheel assembly to each of the sets of arm members 152 (in contrast to one biasing member that connects the arm members 152 directly to each other, as shown in FIG. 5A, FIG. 5B, and FIG. 5C) they will turn the arm members 152 by the same angular displacement since that is the energetically most favorable position.

In an alternative embodiment the biasing member(s) is an actively controlled actuator, such as a linear actuator (lead/ball/roller screw), rack-and-pinion, worm drive, or hydraulic/pneumatic actuator. The advantages of an actively controlled biasing member include the lower likelihood of exerting a force that is too small or too large. If the clamping force is too small the wheels will start to slip on the pipe. If the clamping force is too large it places unnecessary stress on the clamping mechanism and it increases the risk of deforming and/or damaging the pipe, the pipe insulation, or other equipment. With an actively controlled biasing member the force exerted can be adjusted in real time based on sensor values (e.g. wheel slip sensors), based on environmental conditions (e.g. higher clamping force is needed if rain makes the pipes slippery), and/or visual observations from the operator (e.g. lower clamping force is recommended if insulation deformation is observed). An actively controlled biasing member can also facilitate the process of attaching and detaching the robotic apparatus to the pipe, while a passive biasing member necessitates the use of a clamp or similar device to attach and detach the apparatus to the pipe. An actively controlled biasing member can also be designed to exert the appropriate force on a wide range of pipe sizes, while a passive biasing member usually has a more limited range of pipe sizes on which it exerts the appropriate amount of force. The two main disadvantages of an actively controlled biasing member are the following. Firstly, actively controlled actuators typically don't move as fast as passive biasing members. When the robotic apparatus drives around a bend it is especially important to be able to close the clamping mechanism quickly to maintain contact between the wheels and the pipe. Secondly, actively controlled apparatuses are mechanically and electronically more complex, and are therefore more prone to failure.

Figure 17:
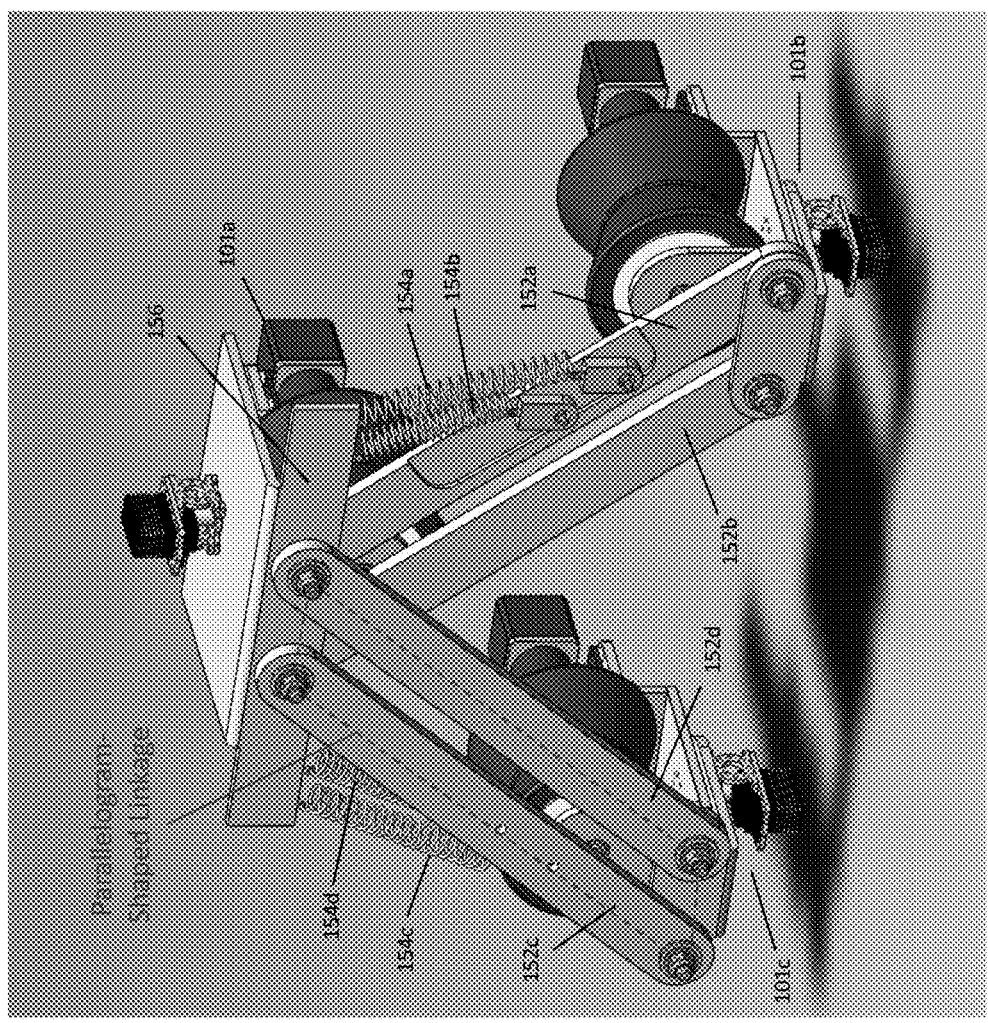
FIG. 17 is a perspective view of a clamping mechanism in accordance with an embodiment of the present disclosure.

Referring ahead to FIG. 17, in another alternative embodiment, one or more biasing members 154 may connect a wheel assembly 101 situated on a first side of pipe 10 with arm member(s) 152 extending to a wheel assembly 101 situated on a second, opposing side of pipe 10, as shown. Of course, in various embodiments, biasing members 154 may additionally or alternatively connect opposing wheel assemblies directly (or even associated structure) to similar effect. For example, in the embodiment of FIG. 17, biasing members 154a, 154b (shown here as tension springs) may connect wheel assembly 101a to arm members 152a, 152b extending to wheel assembly 101b, and biasing members 154c, 154d may connect wheel assembly 101a to arm members 152c, 152d extending to wheel assembly 101c. More specifically, first ends of biasing members 154a, 154b, 154c, 154d each connect to a strut 156 extending longitudinally from wheel assembly 101a, and second ends of biasing members 154a, 154b, 154c, 154d each connect to a mid or distal portion of arm members 152a, 152b, 152c, 152d, respectively. Such an arrangement ensures that the vectors of the associated pulling force generated by biasing members 154a, 154b and biasing members 154c, 154d will act to pull wheel assemblies 101b, 101c, respectively, outwards and upwards relative to wheel assembly 101a (while simultaneously pulling wheel assembly 101a downwards), causing robotic apparatus 100 to compress onto pipe 10 as shown in FIG. 17.

Figure 18:
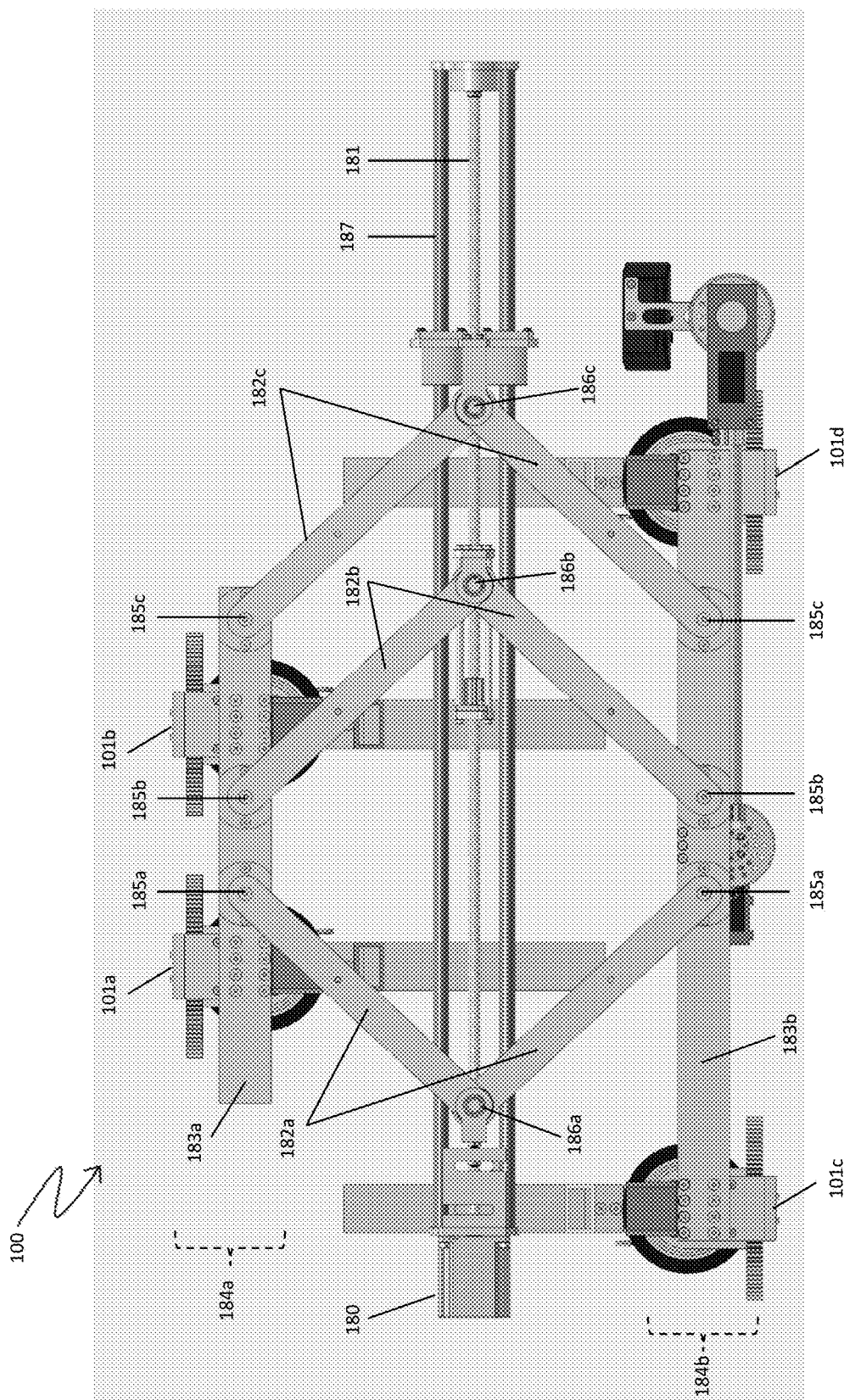
FIG. 18 is a side view of clamping mechanism in accordance with another embodiment of the present disclosure.

FIG. 18 illustrates yet another alternative embodiment of clamping mechanism 150. While this embodiment of clamping mechanism 150 is shown on a four-wheeled robotic apparatus 100, one of ordinary skill in the art will recognize that the present embodiment may be adapted to robotic apparatuses 100 having three wheels or greater than four wheels without diverging from the scope of the present disclosure.

In this embodiment, clamping mechanism 150 may generally include a motor 180 for driving a lead screw 181, which in turn moves a plurality of linear arm pairs 182a, 182b, 182c to expand or compress clamping mechanism 150. More specifically, wheel assemblies 101a and 101b may be coupled to a first frame 183a, thereby defining a first frame assembly 184a, and wheel assemblies 101c, 101d may be coupled to a second frame 183b, thereby defining a second frame assembly 184b. Each of the linear arms 182 may have a first end 185 rotatably coupled to either the first frame 183a or the second frame 183b, and a second end 186 rotatably and slidably coupled to a linear guide 187, as shown. Second ends 186 of at least some of the plurality of linear arms 182 may be operably coupled to lead screw 181 such that rotation of lead screw 181 causes the operably coupled second ends 186 to move from a first position on linear guide 187 to a second position on linear guide 187, thereby changing the angle of each of the linear arms 182 in each pair relative to one another. As the angle between of linear arm 182 of each pair changes, the distance between first frame assembly 184a and second frame assembly 184b is adjusted. For example, driving lead screw 181 in a first direction may cause the operably coupled second ends 186 to move inwards along linear guide 187, causing the angle between the linear arms 182 of each pair to increase as each arm 182 becomes more perpendicular to linear guide 187. This may cause first frame assembly 184a and second frame assembly 184b to move further away from linear guide 187, thereby expanding robotic apparatus 100. Conversely, driving lead screw 181 in a second, opposing direction may cause the operably coupled second ends 186 to move outwards along linear guide 187, causing the angle between the linear arms 182 of each pair to decrease as each arm 182 becomes more parallel to linear guide 187. This may cause first frame assembly 184a and second frame assembly 184b to move closer to linear guide 187, thereby compressing robotic apparatus 100. By adjusting the distance between the first frame assembly 184a and the second frame assembly 184b, clamping mechanism 150 can accommodate various diameter pipes 10 and navigate bends as shown in FIG. 19B and described throughout the present disclosure.

Figure 19A:
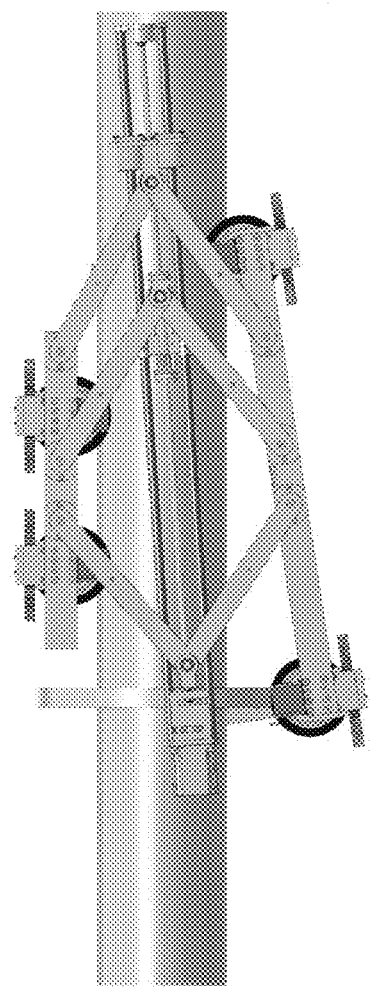
FIG. 19A depicts a robotic apparatus navigating a small protrusion from a pipe in accordance with an embodiment of the present disclosure.
Figure 19B:
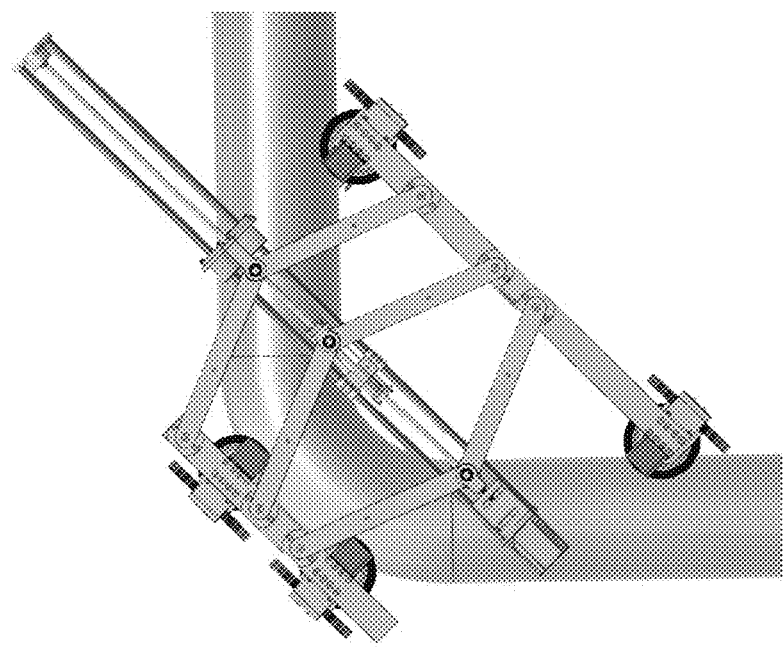
FIG. 19B depicts a robotic apparatus navigating a bend in a pipe in accordance with an embodiment of the present disclosure.

Referring now to FIG. 19A, additionally or alternatively, in an embodiment, less than all of second ends 186 may be operatively connected to lead screw 181. As configured, those second ends 182 not operatively connected to lead screw 181 may freely translate along linear guide 187 and thereby allow at least one of first assembly 184a and second assembly 184b to pivot relative to one another. This, in turn, may allow robotic apparatus to traverse small obstacles protruding from the pipe while maintaining all but one wheel 110 in contact with the surface of pipe 10 at all times. For example, still referring to FIG. 19A, wheel assembly 101c may climb the small protruding obstacle, causing second frame assembly 184b to pivot. This pivoting of second frame assembly 184b allows wheel assembly 101d to remain in contact with the underside of pipe 10. Further, the pivoting of second frame assembly 184b relative to first frame assembly 184a also allows wheel assemblies 101a, 101b to remain in contact with the upper side of pipe 10 while wheel assembly 101c traverses the obstacle. Similarly, frame assemblies 184a, 184b will pivot relative to one another as wheel assembly 101d subsequently traverses the obstacle and thus wheel assemblies 101a, 101b, and 101c will remain in contact with pipe 10.

Traversing Pipeline and Avoiding Obstacles

In operation, robotic apparatus 100 may be mounted on an exterior surface of pipe 10 and traverse pipe 10 to deliver, perform, and/or support various functionalities, such as inspecting pipe 10 for structural defects or corrosion, and sampling the surrounding environment for traces of fluids that may have leaked from pipe 10. In doing so, robotic apparatus 100 may at times may need to reposition itself circumferentially on pipe 10 to, for example, navigate one or more obstacles extending from pipe 10 or to inspect a particular side(s) of pipe 10. Similarly, at times it may be advantageous for robotic apparatus to corkscrew or otherwise follow a helical pattern about the exterior of pipe 10 when attempting to inspect the majority of the exterior of pipe 10 or the surrounding environment. Accordingly, robotic apparatus 100 of the present disclosure may be configured to traverse pipe 10 along straight and helical paths. Generally speaking, travel along these paths may be accomplished by driving one or more of wheels 110 using motor(s) 130 and steering wheels 110 using alignment mechanisms 120, as further described in more detail below.

To follow a straight path along pipe 10, alignment mechanisms 120 may orient wheels 110 to be aligned with the longitudinal axis of pipe, as shown in FIG. 5A, FIG. 5B and FIG. 5C. As configured, the hourglass shape (if equipped) may center wheels 110 on opposing sides of pipe 10 and steer robotic apparatus along a straight path such that wheels 110 continue following those particular opposing sides (e.g., the top and bottom of pipe 10 as shown).

Referring now to FIG. 7, FIG. 8A, FIG. 8B, FIG. 8C, FIG. 8D, FIG. 8E, and FIG. 8F, to follow a helical path, whether for the purposes of following a helical inspection pattern or simply to reposition robotic apparatus about the circumference of pipe 10, alignment mechanisms 120 may adjust the orientation of wheels 110 rotationally relative to yaw axis 103 of robotic apparatus 100, which in the present embodiment coincides with engagement plane 104. Alignment mechanisms 120, in various embodiments, may adjust the orientation of wheels 110 rotationally (i.e., clockwise or counter-clockwise). For example, in an embodiment, alignment mechanism 120 may adjust the orientation of wheels 110 to the left to guide robotic apparatus 100 along a helical path with coils moving in a counterclockwise direction about the circumference of pipe 10. Likewise, alignment mechanism 120 may adjust the orientation of wheels 110 to the right to guide robotic apparatus 100 along a helical path with coils moving in a clockwise direction about the circumference of pipe 10.

Alignment mechanisms 120, in various embodiments, may also adjust the orientation of wheels 110 to any suitable degree to control a pitch of the resulting helical path. For example, adjusting the orientation of wheels 110 to the left or right by a small amount (e.g., 5 degrees) may cause the resulting helical pathway to have a large pitch (i.e., large distance between adjacent coils), while adjusting the orientation of wheels 110 to the left or right by a large amount (e.g., 30 degrees) may cause the resulting helical pathway to have a small pitch (i.e., small distance between adjacent coils). Alignment mechanism 120, in various embodiments, may be configured to adjust the orientation of wheels 110 by up to 89 degrees relative to a longitudinal axis of pipe 10 and still follow a helical pattern; however, alignment mechanism 120 may more preferably be configured to adjust the orientation of wheels 110 from center by between about 1 degree and about 60 degrees. The greater the angle to which the wheels 110 are turned, the further apart the contact areas move on the wheel surface 112. In other words, if the wheel 110 is to stay in contact with the pipe 10 (and not only contact along the outer rims of the wheels 110) the total width of the wheel 110, the and the diameter of the pipe 10 put an upper limit on the angle to which the wheel 110 can be turned.

Referring now to FIG. 9A, FIG. 9B, FIG. 9C, FIG. 9D, FIG. 9E, FIG. 9F, FIG. 9G, FIG. 9H, FIG. 10A, FIG. 10B, FIG. 10C, FIG. 11A, FIG. 11B, FIG. 11C, FIG. 11D, FIG. 12A, FIG. 12B, FIG. 12C, and FIG. 12D, robotic apparatus 100, in various embodiments, may be repositioned about the circumference of pipe 10 to navigate past various obstacles, as described in more detail below.

Figure 9E:
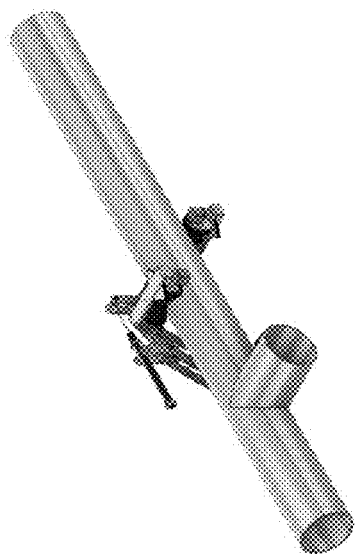
Figure 9F:
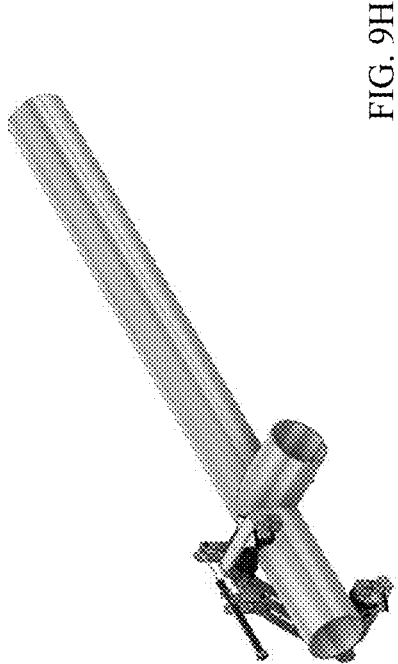
Figure 9G:
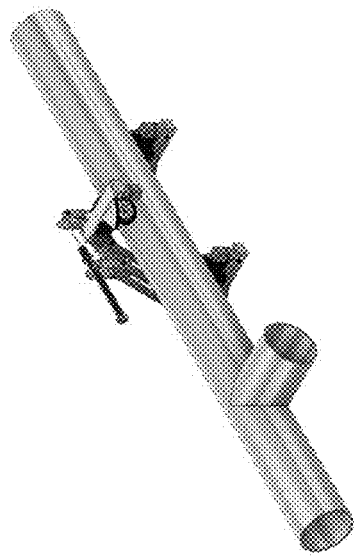
Figure 9H:
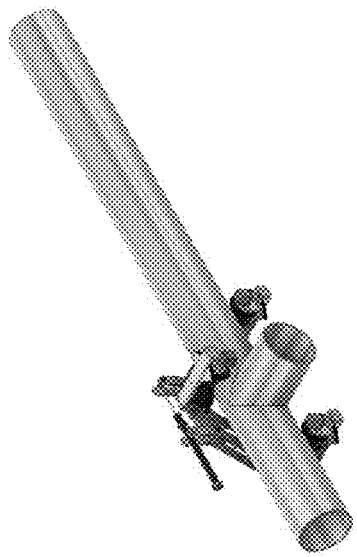

FIG. 9A, FIG. 9B, FIG. 9C, FIG. 9D, FIG. 9E, FIG. 9F, FIG. 9G, and FIG. 9H illustrate a representative approach for navigating a large unidirectional protrusion from pipe 10 such as pipe junctions and pipe supports using robotic apparatus 100. In FIG. 9A robotic apparatus 100 approached a large protruding obstacle. Its orientation is not suitable to pass the obstacle and it will go through the procedure to rotate to a suitable orientation for passing the obstacle. In FIG. 9B the robot has turned its wheels in place (to about 45 degrees) using the alignment mechanism that was described earlier in this disclosure. It turns the wheels so that it can commence the helical movement needed to change its orientation with respect to the pipe. In FIG. 9C it is starting to travel in a helical pathway along the pipe with the wheels kept at the same angle as in FIG. 9B. FIG. 9D shows the robot as it keeps driving in a helical pathway. It drives along the longitudinal axis and around the circumference of the pipe at the same time. In FIG. 9E the robot has reach the preferred orientation with respect to the obstacle. The open side of the robot is on the same side of the pipe as the obstacle. FIG. 9F shows how the robot employs the alignment mechanism to turn the wheels back to the default position, where the direction of travel is parallel with the longitudinal axis of the pipe. Once it is in the preferred orientation the robot keeps driving straight to pass the obstacle. FIG. 9G shows the robot as it starts to pass the obstacle and the obstacle protrudes through the open side of the robot. FIG. 9H shows how the robot has passed the obstacle and it returns to its normal operation.

Figure 10C:
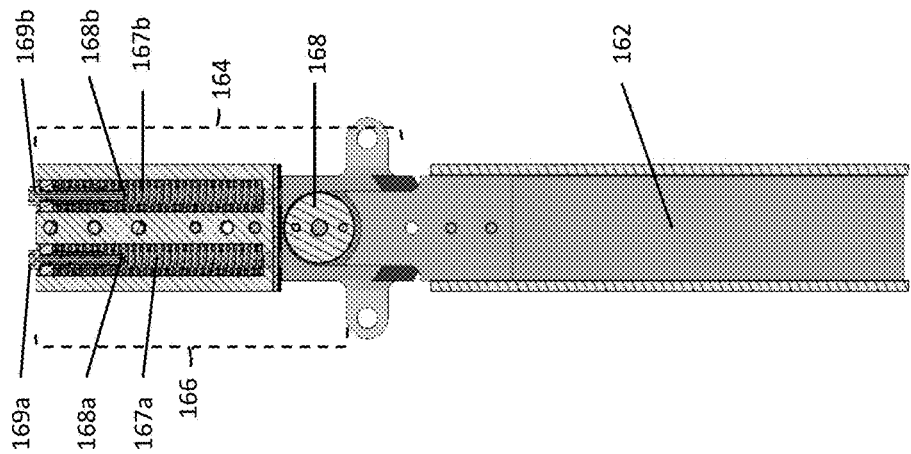
FIG. 10A, FIG. 10B, and FIG. 10C depict a fail-safe mechanism in accordance with an embodiment of the present disclosure.
Figure 10B:
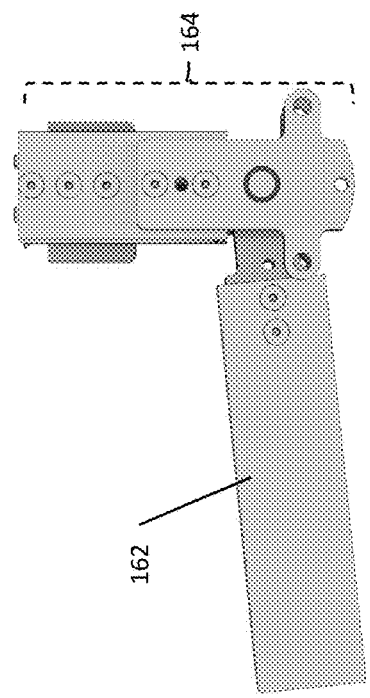
Figure 10A:
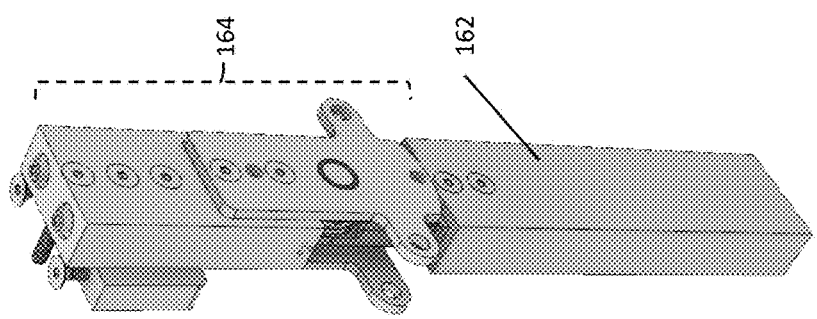

FIG. 10A, FIG. 10B, and FIG. 10C depict various views of a mechanism 160 for preventing robotic apparatus 100 from falling off of pipe 10 should robotic apparatus 100 decoupled from pipe 10. Also referred to herein as a "fail-safe mechanism", mechanism 160 may extend from one or more of wheel assemblies 101 and across open side 102 of robotic apparatus 100, such that robotic apparatus 100 effectively surrounds pipe 10 on all sides as shown in FIG. 11A, FIG. 11B, FIG. 11C, and FIG. 11D. As configured, should wheels 110 slip or otherwise disengage from pipe 10, robotic apparatus 100 will remain connected to pipe 10 in a manner that prevents it from falling to the ground and being damaged or destroyed.

Referring first to FIG. 10A, mechanism 160 may generally comprise an arm member 162 and a rotating joint 164. In various embodiments, rotating joint 164 forms a proximal portion of fail-safe mechanism 160, and is coupled to or forms part of wheel assembly 101. Arm member 162 may be coupled to or be integrally formed as part of rotating joint 164, and may extend across open side 102 of robotic apparatus 100 in a neutral state. To allow for a large protrusion or other obstacle to pass through open side 102 of robotic apparatus 100, rotating joint 164 may be configured to rotate within the plane of open side 102 in response to forces applied to arm member 162 by the obstacle as robotic apparatus traverses a corresponding section of pipe 10. Stated otherwise, upon coming into contact with the obstacle, arm member 162 may passively sweep rearwards about a pivot point defined by rotating joint 164 until the obstacle has passed beyond the reach of arm member 162, as shown in FIG. 10B. Upon clearing the obstacle, arm member 162 may automatically sweep forward to return to the neutral state, where it again extends across open side 102 to prevent robotic apparatus 100 from falling should wheels 110 decouple from pipe 10.

To that end, rotating joint 164, in various embodiments, may include a biasing mechanism 166, such as torsion spring or other mechanism/assembly configured to apply a restorative force for returning arm member 162 to the neutral state after an obstacle is passed. In the embodiment shown in FIG. 10C, biasing mechanism 166 includes an assembly of linear springs 167a, 167b connected to a pulley assembly 168. In particular, springs 167a, 167b may be the same or substantially similar to one another, and may be arranged side-by-side and extend from a proximal end of fail-safe mechanism 160 towards pulley assembly 168. Pulley assembly 168 may include a pulley connected to springs 167a, 167b by a cable, wire, string, or other such connector (collectively, "cable" hereinafter). A first end 168a of the cable may extend axially through spring 167a and connect to a cap 169a positioned at a proximal end of spring 167a, and likewise a second end 168b of the cable may extend axially through spring 167b and connect to a cap 169b positioned at a proximal end of spring 167b. As configured, when arm member 162 (and by extension pulley 169), is swept clockwise this figure, pulley assembly 168 may pull cable end 168b (and attached cap 169b) downwards, thereby progressively compressing spring 167b. This in turn builds up a restoring force in spring 167b that generates a counterclockwise moment for sweeping arm member 162 counterclockwise in this figure back to the neutral state when the obstacle has cleared arm member 162. Likewise, when arm member 162 (and by extension pulley assembly 168), is swept counterclockwise in this figure, pulley assembly 168 may pull cable end 168a (and attached cap 169a) downwards, thereby progressively compressing spring 167a. This in turn builds up a restoring force in spring 167a that generates a clockwise moment for sweeping arm member 162 clockwise in this figure back to the neutral state when the obstacle has cleared arm member 162.

Notably, rotating joint 164, in various embodiments, may be constrained to rotation within the plane of open side 102 only, and thus not permitted to rotate transverse to (e.g., away from or towards pipe 10) said plane, such that fail-safe mechanism 160 does not permit pipe 10 to pass through open side 102 in the event robotic apparatus 100 were to decouple from pipe 10.

Figure 11A:
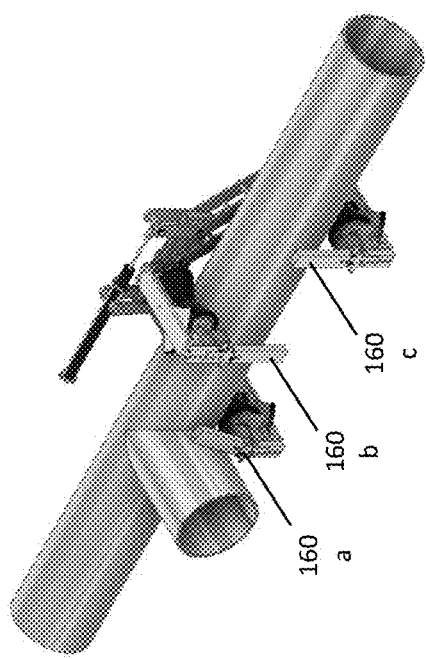
FIG. 11A, FIG. 11B, FIG. 11C, and FIG. 11D illustrate a fail-safe mechanism allowing passage of an obstacle in accordance with an embodiment of the present disclosure.
Figure 11B:
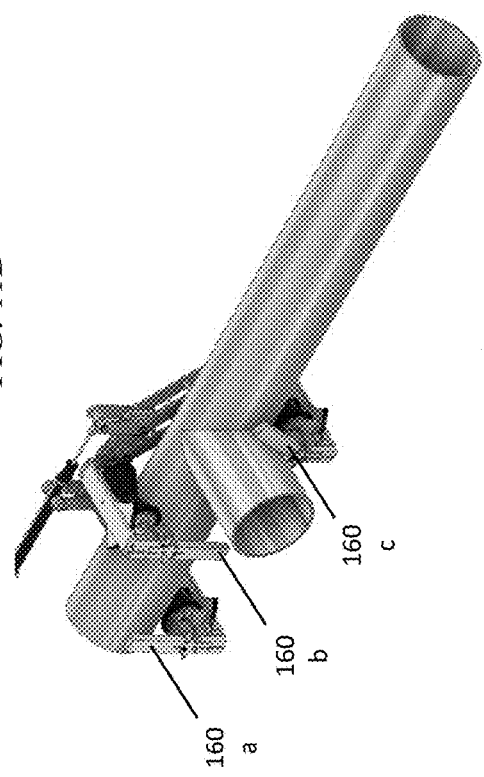
Figure 11C:
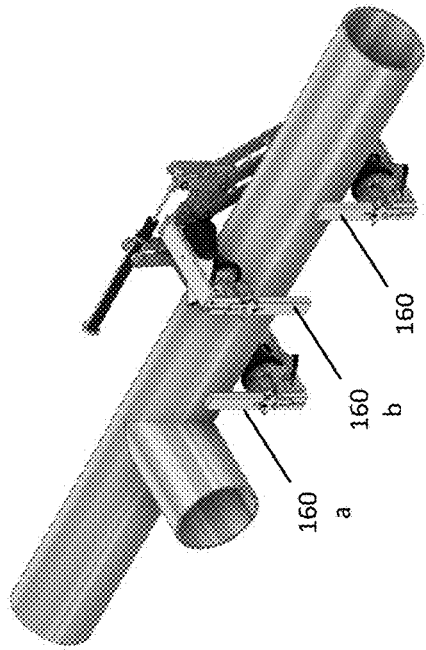
Figure 11D:
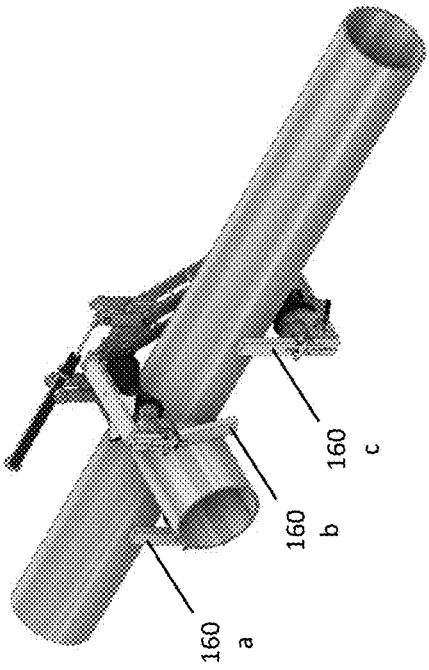

FIG. 11A, FIG. 11B, FIG. 11C, and FIG. 11D illustrate a representative approach for navigating a large unidirectional protrusion from pipe 10 such as pipe junctions and pipe supports when robotic apparatus 100 is equipped with fail-safe mechanism 160. FIG. 11A shows robotic apparatus 100 as it approaches an obstacle protruding from pipe 10. In this figure, robotic apparatus 100 is already in the preferred orientation for passing the protruding obstacle—that is, open side 102 is aligned with the protruding obstacle. It drives straight ahead, parallel to the longitudinal axis of the pipe. In FIG. 11B, robotic apparatus 100 starts to pass the obstacle and the failsafe mechanism 160a attached to the first wheel assembly has hit the protrusion. Since arm member 162 is free to rotate in this plane it starts to pivot as it gets pushed by the protruding obstacle. In FIG. 11C, the first failsafe mechanism 160 has completely passed the obstacle and biasing member 166 has returned arm member 162 to its neutral state. The middle failsafe mechanism 160b is now passing the protruding obstacle. FIG. 11D shows how the middle failsafe mechanism 160b has cleared the obstacle and returned to its neutral position. The last failsafe mechanism 160c is now contacting the protruding obstacle. Once the last wheel assembly passes the obstacle the last failsafe mechanism 160c will swing back to the neutral safe position and robotic apparatus 100 is free to return to its normal operation.

Figure 12A:
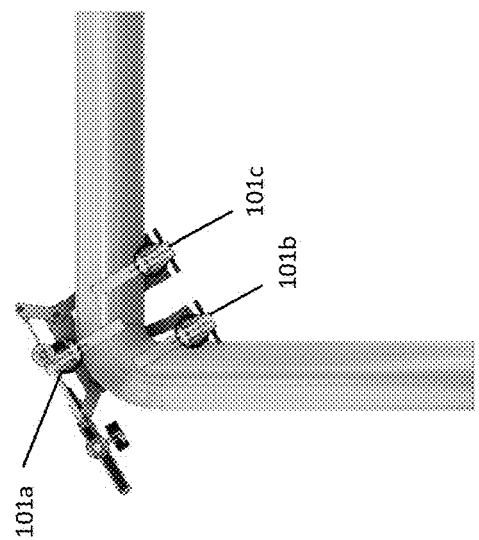
FIG. 12A, FIG. 12B, FIG. 12C, and FIG. 12D illustrate the robotic apparatus navigating a bend in a pipe in accordance with an embodiment of the present disclosure.
Figure 12B:
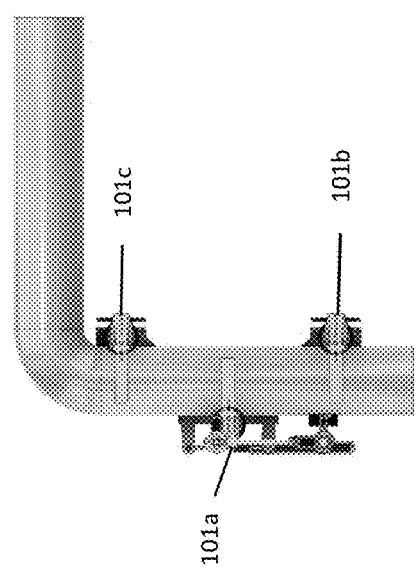
Figure 12C:
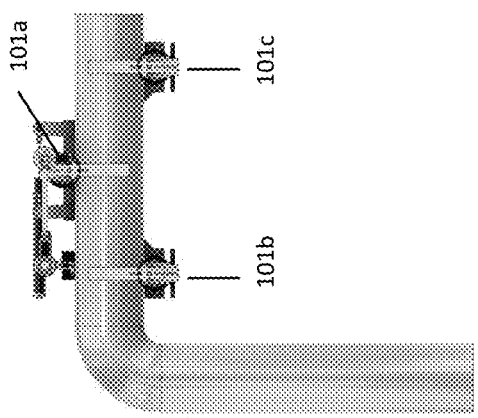
Figure 12D:
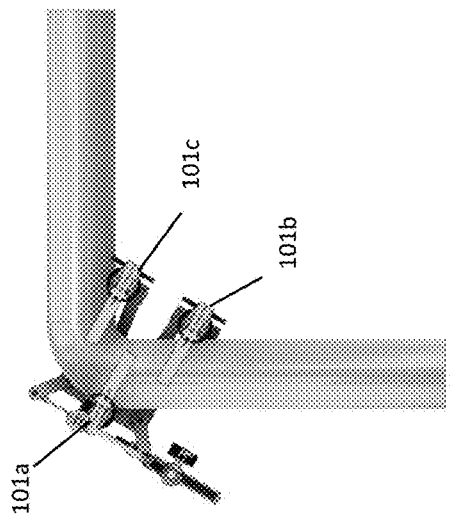

FIG. 12A, FIG. 12B, FIG. 12C, and FIG. 12D illustrate a representative approach for navigating a bend or curve in pipe 10 using robotic apparatus 100. FIG. 12A shows the ideal orientation of the robotic apparatus 100 as it approaches the bend. The depicted embodiment of robotic apparatus 100 is designed to traverse the bend with the single wheel assembly 101a driving along the outer centerline of the bend and the two wheel assemblies 101b, 101c on the opposing side to drive along the inner centerline of the bend. Alternative embodiments have been designed so that the single wheel assembly 101a can drive along the inside of the bend and the two wheel assemblies 101b, 101c can drive along the outside of the bend. However, these two different approaches place different constraints on the range of motion of the clamping mechanism 150, and a single embodiment is typically designed to employ one of the two approaches. FIG. 12B shows how the robotic apparatus 100 enters the bend. As shown, robotic apparatus 100 has to expand significantly as it drives towards the apex of the bend. The outside wheel in wheel assembly 101a will speed up as it enters the bend to compensate for the longer path length compared to the other wheels. In FIG. 12C, robotic apparatus 100 has passed the apex of the bend. At this stage clamping mechanism 150 gradually contracts to keep the wheels 110 in contact with the surface of the pipe 10 and the outside wheel 110a gradually returns to the same speed as the other wheels 110b, 110c, as the path length difference diminishes. In FIG. 12D, robotic apparatus 100 has completely passed the bend and it returns to its normal operation.

Pipeline Inspection and Other Payloads

Figure 13B:
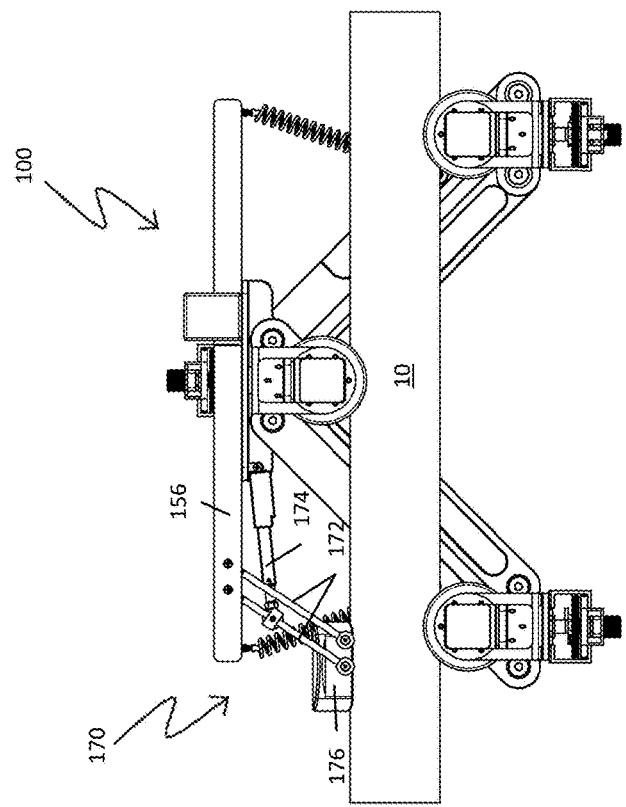
FIG. 13A and FIG. 13B depict a sensor assembly in a lowered and raised position in accordance with an embodiment of the present disclosure.
Figure 13A:
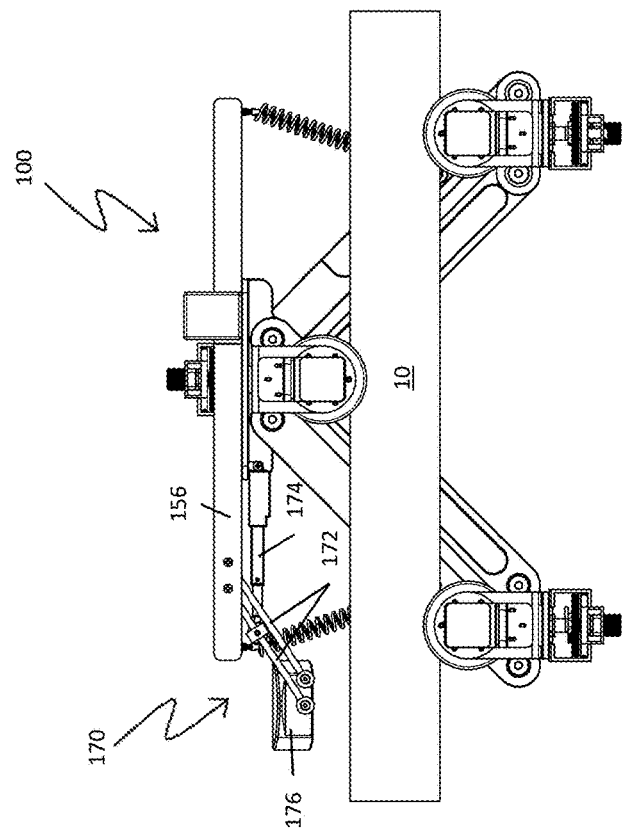

FIG. 13A and FIG. 13B illustrate an embodiment of robotic apparatus 100 including a sensor assembly 170 for performing structural inspections of pipe 10. Sensor assembly 170, in various embodiments, may generally include one or more arms 172 and an actuator 174 for positioning a sensor 176 relative to pipe 10.

Sensor 176, in various embodiments, may include one of a variety of sensors suitable for inspecting or otherwise gathering information concerning pipe 10 and/or the surrounding environment. For example, in an embodiment, sensor 176 may include an ultrasonic sensor or other sensor suitable for non-destructive inspection (NDI) of structural aspects of pipe 10, such as measuring wall thickness or detecting cracks/corrosion. In another embodiment, sensor 176 may include a sensor configured to sample air proximate to pipe 10 for traces of fluids (e.g., natural gas, oil) that may have leaked out of pipe 10. Such traces may be indicative of cracks or corrosion in pipe 10, and thus may be used for structural inspection purposes. While sensor assembly 170 of the present disclosure may be described in the context of positioning a sensor 176 for pipeline inspection purposes, it should be recognized that any sensor 170 may be used in connection with sensor assembly 170 for any suitable purpose.

Arm(s) 172, in various embodiments, may couple sensor 176 to robotic apparatus 100 and be moved to position sensor 176 relative to pipe 10. In particular, a first end of arm(s) 172 may be rotatably coupled to robotic apparatus 100, for example, on strut 156 as shown. As configured, arm(s) 172 may be pivoted up and down on strut 156 and thereby position sensor 176 away from or close to pipe 10, respectively. In an embodiment (shown), the second end of arm(s) 172 may also be rotatably coupled to sensor 176, thereby allowing sensor 176 to pivot relative to arm(s) 172 and thus remain parallel to the surface of pipe 10 if desired or necessary for sensor 176 to function optimally. FIG. 13A illustrates sensor assembly 170 in a raised position and FIG. 13B illustrates sensor assembly in a lowered position. Arm(s) 172, in an embodiment, may be used to raise sensor 176 to a position away from pipe 10 when measurements are not needed and/or to prevent sensor 176 from colliding with an obstacle along pipe 10. Conversely, arm(s) 172, in an embodiment, may be used to lower sensor 176 to a position close to or against pipe 10 for taking measurements.

Actuator 174, in various embodiments, may be used to move arm(s) 172 in positioning sensor 176. Actuator 174 may include any actuator, motor, and associated assemblies (e.g., pulleys, gear trains). In the exemplary embodiment shown, actuator 174 includes a linear actuator having a proximal end rotatably coupled to wheel assembly 101a of robotic apparatus 100 and having a distal end coupled to arm(s) 172, and specifically here to a cross-bar member extending between arms 172 that freely rotates to maintain alignment with linear actuator 172, as shown, regardless of whether linear actuator 172 is in an extended or retracted position. Of course, one of ordinary skill in the art will recognize alternative actuators that may be suitable for the described purpose within the scope of the present disclosure. For example, in another embodiment (not shown), actuator 174 may include a motor configured to wind in/out a cable or pulley assembly positioning arm(s) 172 and sensor 176 coupled thereto.

Figure 14B:
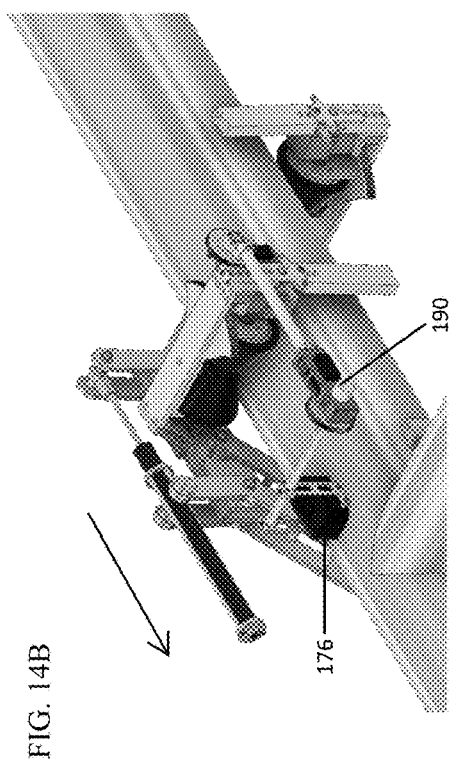
FIG. 14A, FIG. 14B, FIG. 14C, and FIG. 14D depict another sensor assembly in accordance with an embodiment of the present disclosure.
Figure 14D:
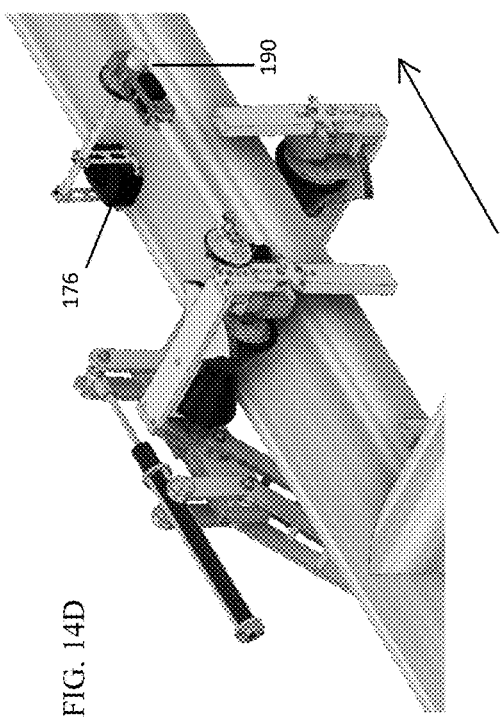
Figure 14A:
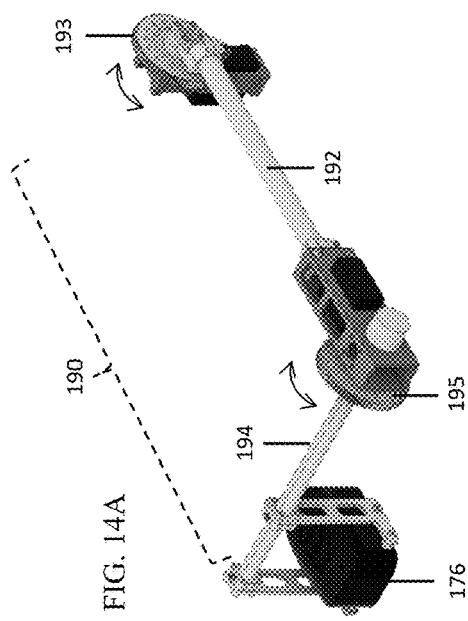
Figure 14C:
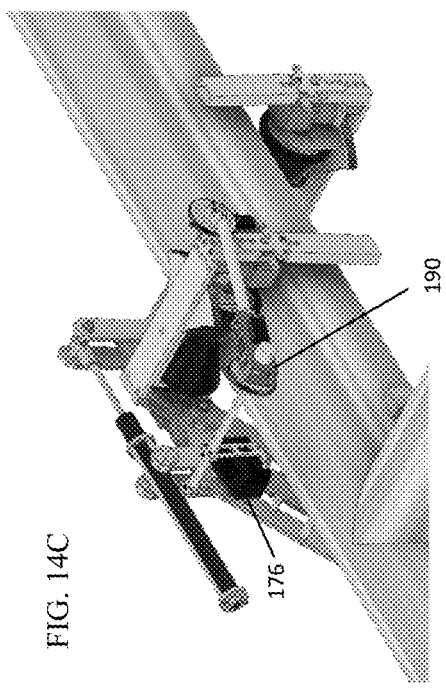
Figure 15A:
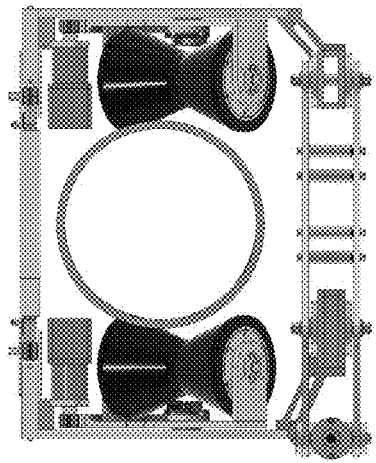
FIG. 15A, FIG. 15B, FIG. 15C, and FIG. 15D depict a robotic apparatus translating to account for wheel slip in accordance with an embodiment of the present disclosure.
Figure 15B:
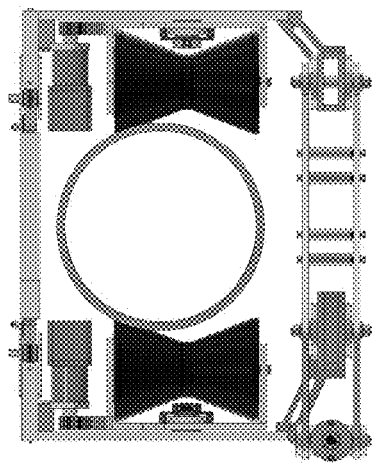
Figure 15C:
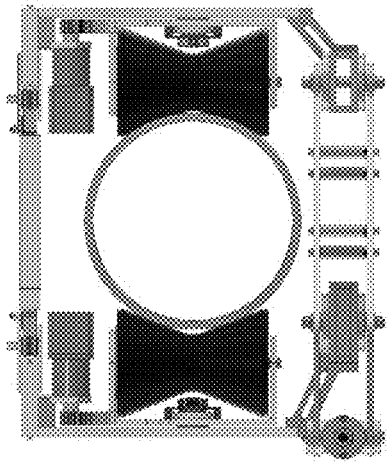
Figure 15D:
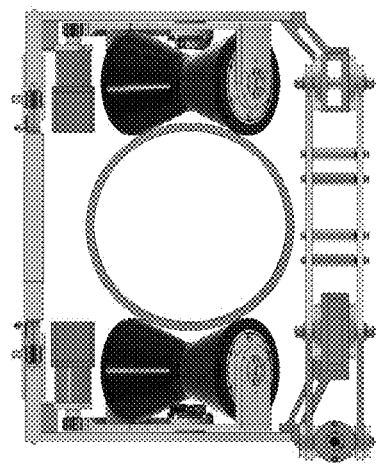

FIG. 14A, FIG. 14B, FIG. 14C, and FIG. 14D depict another embodiment of sensor assembly 170, which generally includes sensor 176, and an articulated arm 190 comprising a first arm segment 192 and a second arm segment 194. A proximal end of first arm segment 192 may be rotatably coupled by a first rotating joint 193 to robotic apparatus 100 such that articulated arm 190 may be rotated relative to robotic apparatus 100. A proximal end of second arm segment 194 may be rotatably coupled by a second rotating joint 195 to a distal end of first arm segment 192 such that second arm segment 194 may be rotated relative to first arm segment 192. Each rotating joint 193, 195, in various embodiments, may be motorized and configured for independent rotation from one another. As configured, first rotating joint 193 may raise or lower articulated arm 190 relative to pipe 10 and second rotating joint 195 may independently adjust an orientation of sensor 176 relative to the surface of pipe 10, as shown in FIG. 14A and FIG. 14C.

Further, first rotating joint 193 may be rotated to a greater extent for positioning articulated arm 190 out in front of either end of robotic apparatus 100, as shown in FIG. 14B and FIG. 14D. As configured, sensor 176 may be positioned to take measurements in front of robotic apparatus 100 regardless of its direction of travel on pipe 10. In one aspect, this configuration may provide for more accurate measurements, as robotic apparatus 100 would not yet be in contact with the portion of pipe 10 being inspected with sensor 176, which may otherwise produce vibrations, cause a dampening effect, or otherwise affect structural properties of the portion of pipe 10 being inspected. In another aspect, by positioning sensor assembly out in front of robotic apparatus 100 (again, regardless of the direction of travel), it may be possible to inspect portions of pipe 10 all the way up to an upcoming obstacle. Contrast this with only being able to inspect only those portions of pipe 10 more than a length of robotic apparatus away from the upcoming obstacle because sensor assembly 170 is positioned behind robotic apparatus 100.

Figure 20:
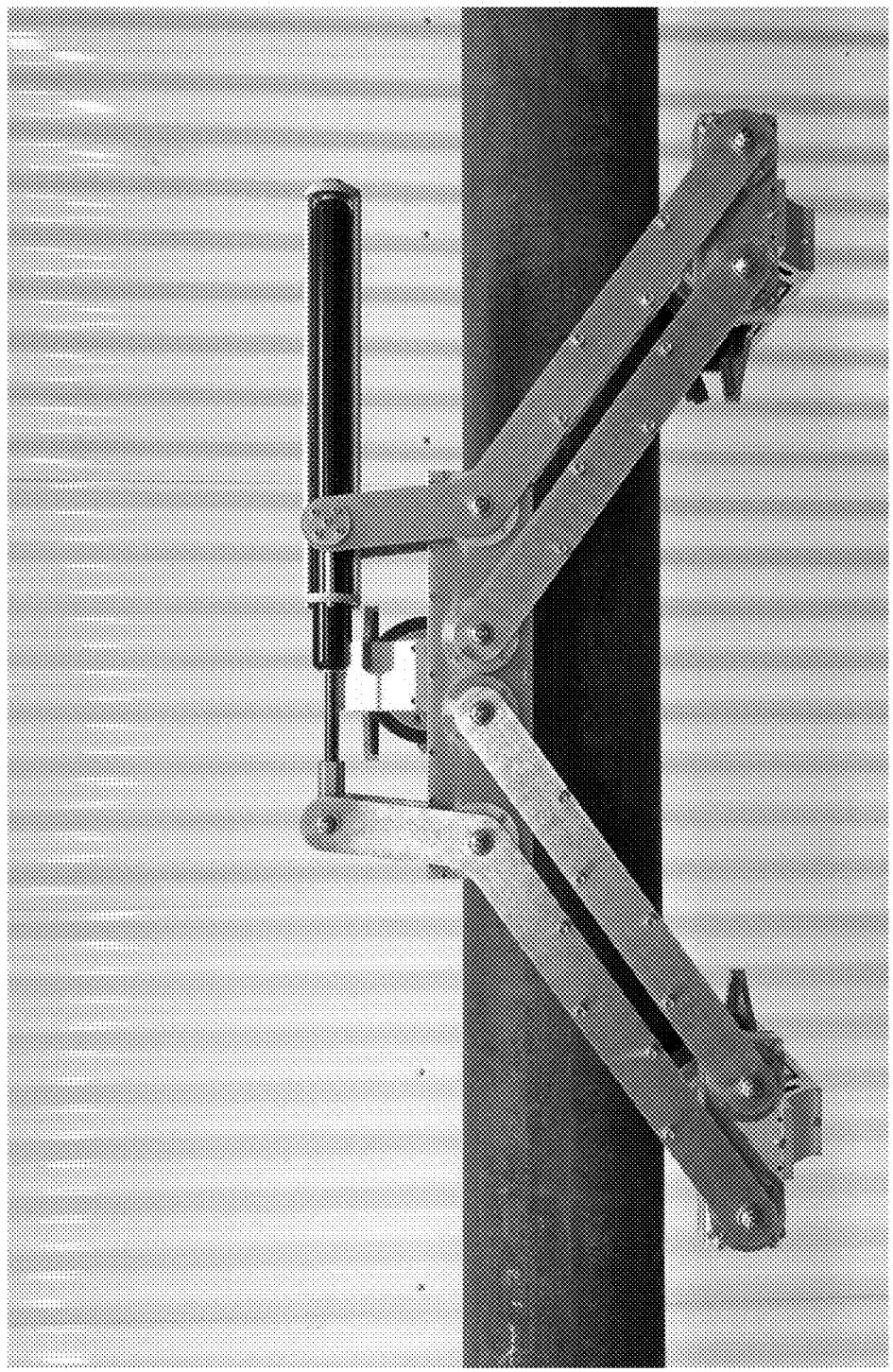
FIG. 20 and FIG. 21 depict side views of the prototype of robotic apparatus 100, with wheels 110 aligned for straight travel along pipe 10, in accordance with an embodiment of the present disclosure.
Figure 21:
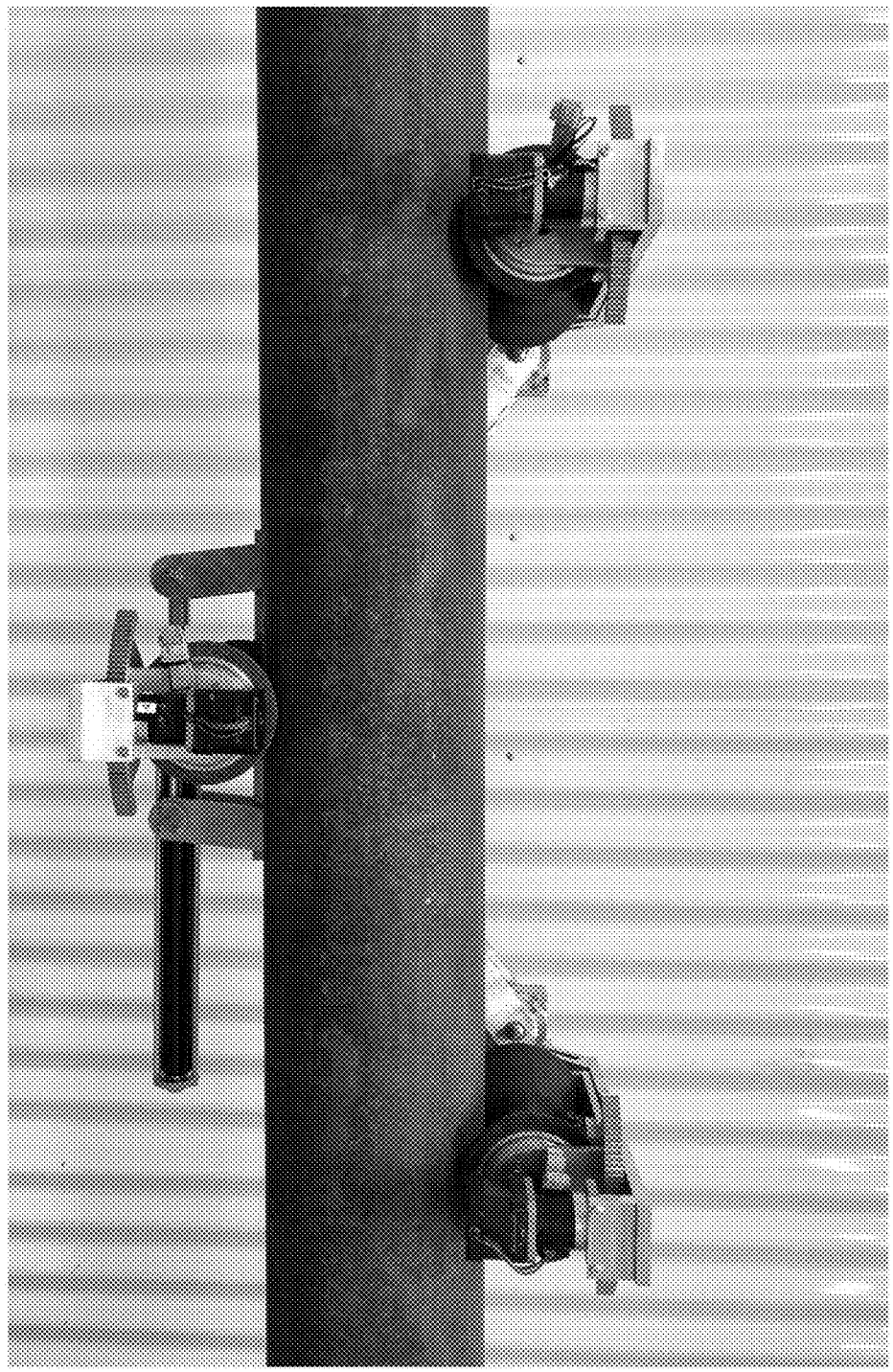
Figure 22:
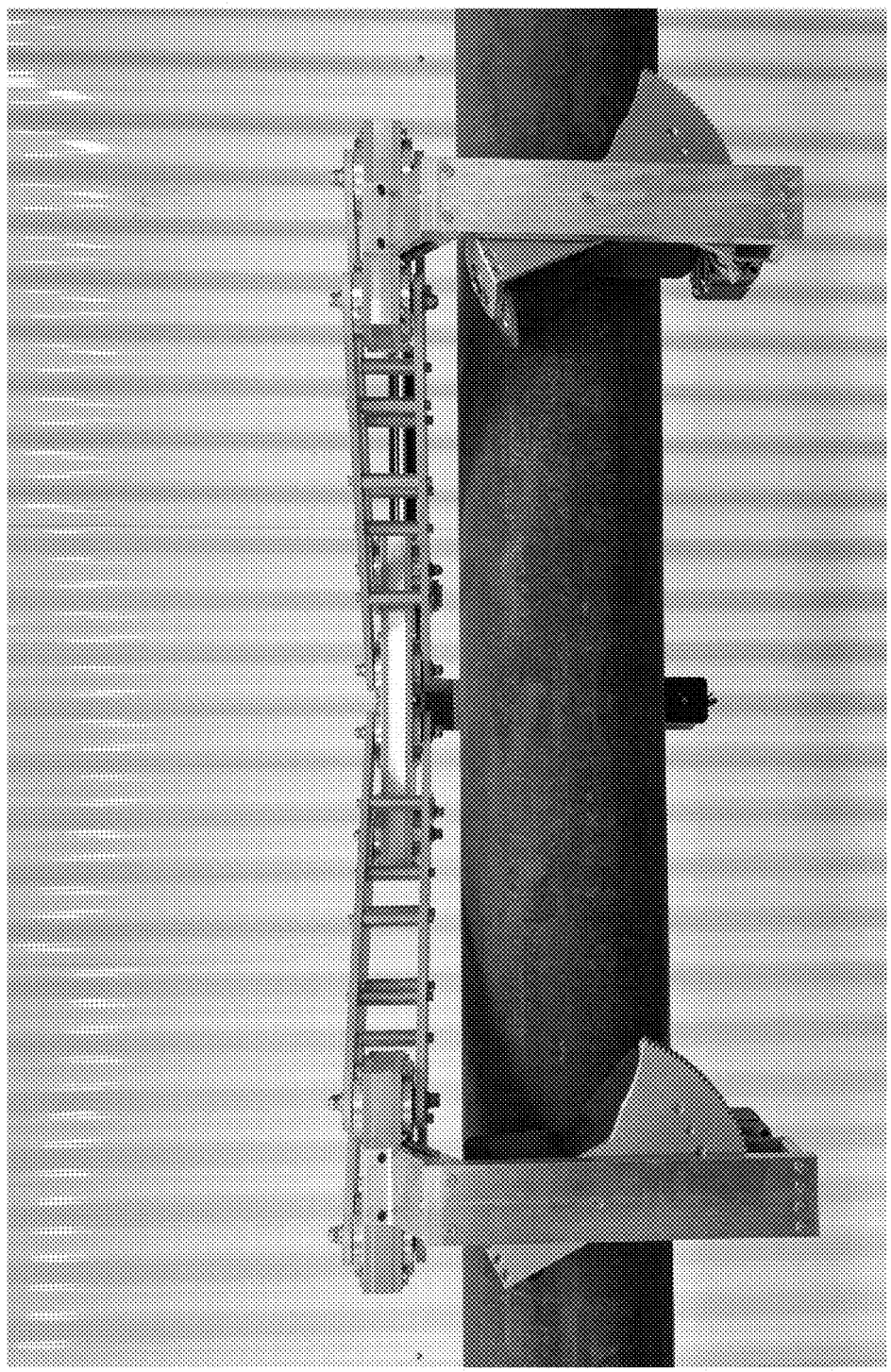
FIG. 22 depicts a bottom view of the prototype of robotic apparatus 100, with the orientation of wheels 110 adjusted for helical travel along pipe 10 in accordance with an embodiment of the present disclosure.
Figure 23:
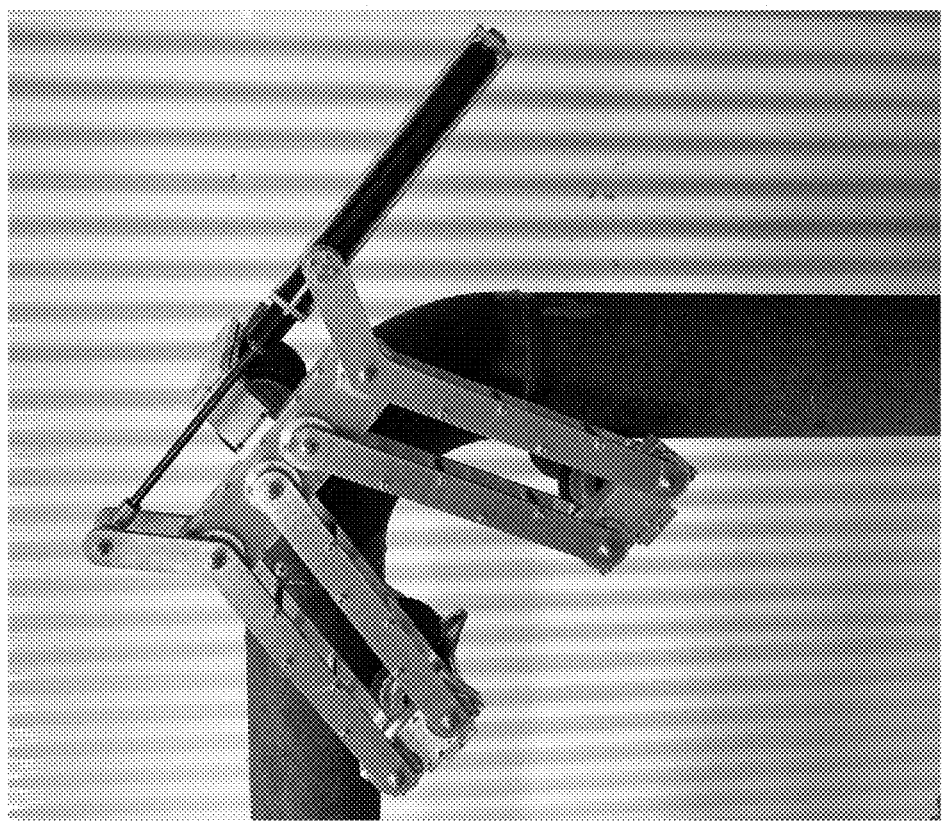
FIG. 23 depicts a side view of the prototype of robotic apparatus 100 navigating a bend in pipe 10 in accordance with an embodiment of the present disclosure.
Figure 24:
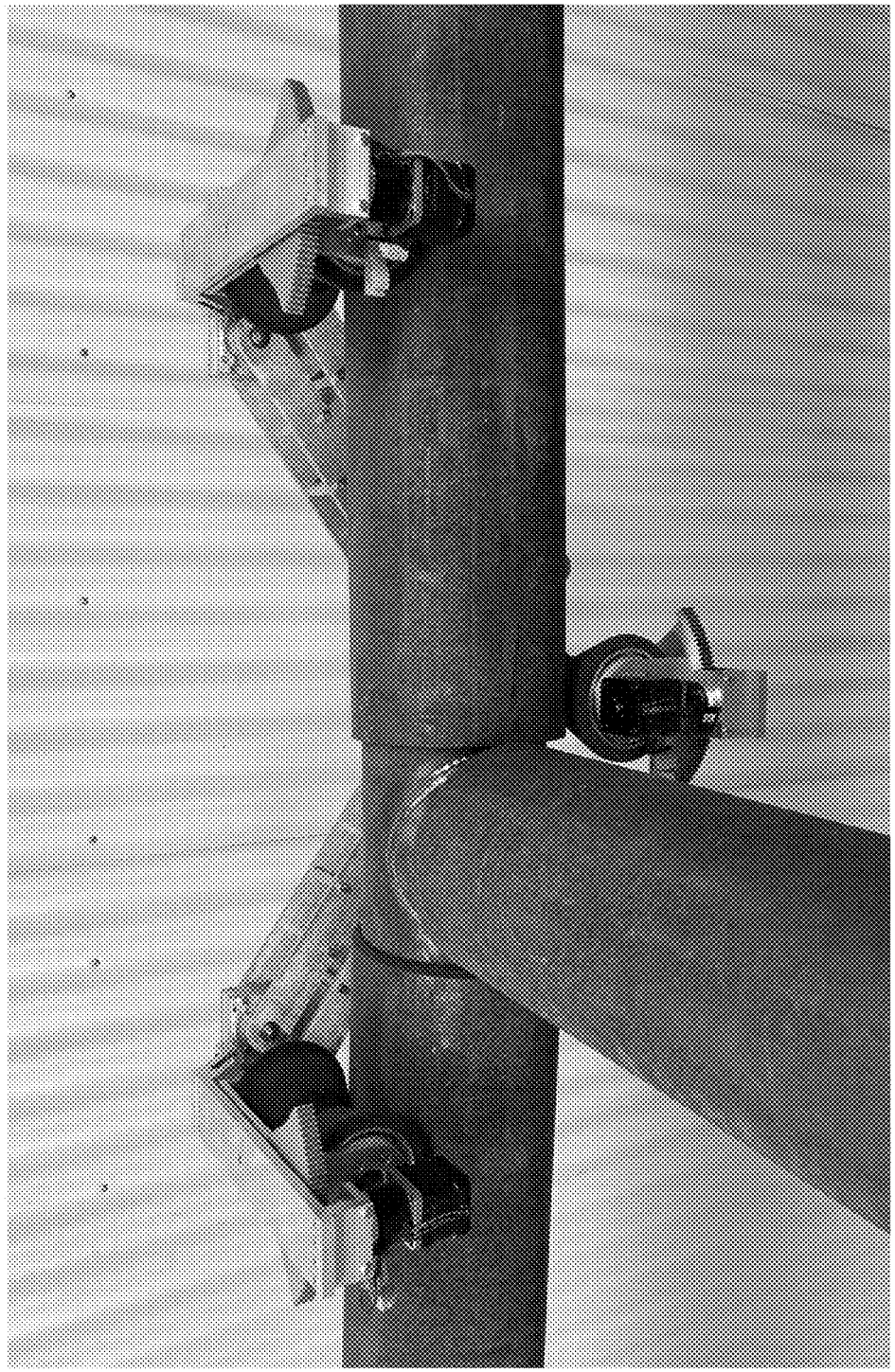
FIG. 24 depicts a side view of the prototype of robotic apparatus 100, with open side 102 positioned for passing an obstacle protruding from pipe 10 in accordance with an embodiment of the present disclosure.

FIG. 20, FIG. 21, FIG. 22, FIG. 23, and FIG. 24 are photographs of a prototype of a representative embodiment of robotic apparatus 100 for further illustrative purposes. FIGS. 20 and 21 depict side views of the prototype of robotic apparatus 100, with wheels 110 aligned for straight travel along pipe 10. FIG. 22 depicts a bottom view of the prototype of robotic apparatus 100, with the orientation of wheels 110 adjusted for helical travel along pipe 10. FIG. 23 depicts a side view of the prototype of robotic apparatus 100 navigating a bend in pipe 10. FIG. 24 depicts a side view of the prototype of robotic apparatus 100, with open side 102 positioned for passing an obstacle protruding from pipe 10.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A robotic apparatus, comprising:
   a first wheel assembly including a wheel and an alignment mechanism, and configured for positioning on a first side of a pipe;
   a second wheel assembly and a third wheel assembly, each including a wheel and an alignment mechanism, and configured for positioning on a second, opposing side of the pipe; and
   a clamping mechanism configured to apply a force for urging the second wheel and the third wheel to pivot in opposing directions towards a plane of the first wheel for securing the first wheel, the second wheel, and the third wheel to the pipe,
   wherein the alignment mechanisms are configured for selectably adjusting an orientation of the wheels to allow the robotic apparatus to move along a straight path or a helical path on the pipe.

2. The robotic apparatus of claim 1, wherein at least one of the wheels has a concave shaped surface for engaging the pipe.

3. The robotic apparatus of claim 1, wherein at least one of the wheel assemblies includes a motor for rotating the wheel of the corresponding assembly.

4. The robotic apparatus of claim 3, wherein the motor is situated inside of the wheel of the corresponding assembly.

5. The robotic apparatus of claim 1, wherein the clamping mechanism includes one or more biasing members for generating the pulling force.

6. The robotic apparatus of claim 5, wherein the one or more biasing members are configured to passively generate the pulling force.

7. The robotic apparatus of claim 5, wherein the one or more biasing members includes at least one of a tension spring, a compression spring, and a torsion spring.

8. The robotic apparatus of claim 1, wherein the one or more biasing members are configured to actively generate the pulling force.

9. The robotic apparatus of claim 1, wherein the clamping mechanism includes:
   a first arm member connecting the first wheel assembly with the second wheel assembly;
   a second arm member connecting the first wheel assembly with the third wheel assembly; and
   one or more biasing members for applying a pulling force to engage the wheels on opposing sides of the pipe, the one or more biasing members either connecting the first arm member to the second arm member or connecting the first wheel assembly to the first arm member and to the second arm member.

10. The robotic apparatus of claim 9,
    further including a third arm member and a fourth arm member arranged parallel and adjacent to the first arm member and the second arm member, respectively, thereby forming first and second parallelogram-shaped linkages between the first wheel assembly and the second wheel assembly and between the first wheel assembly and the third wheel assembly, respectively,
    wherein the parallelogram-shaped linkages maintain the wheel assemblies in parallel alignment with one another regardless of a relative position of the wheel assemblies to one another.

11. The robotic apparatus of claim 1, wherein the clamping mechanism is offset from and parallel to a plane shared by the wheels.

12. The robotic apparatus of claim 11, comprising an open side situated opposite the clamping mechanism, through which an obstacle extending from the pipe may pass unobstructed.

13. The robotic apparatus of claim 12, further including one or more members configured to extend across the open side of the robotic apparatus to prevent the robotic apparatus from falling off the pipe.

14. The robotic apparatus of claim 13, wherein the one or more members are configured to pivot along a plane of the open side to accommodate passage of an obstacle through the open side of the robotic apparatus.

15. The robotic apparatus of claim 1, wherein the alignment mechanism is configured to adjust the orientation of a corresponding wheel in a rotational direction relative to an axis that is normal to the pipe.

16. The robotic apparatus of claim 15, wherein adjusting the orientation of the wheels rotationally causes the robotic apparatus to move along a helical path along the pipe.

17. The robotic apparatus of claim 1, the alignment mechanism comprises:
    a wheel frame to which the wheel is rotatably coupled about a first axis;

a base plate to which the wheel frame is rotatably coupled about a second axis orthogonal to the first axis; and a motor configured to rotate the wheel frame about the second axis, thereby adjusting the orientation of the wheel relative to the base plate.

18. The robotic apparatus of claim 1, further including a sensor assembly for inspecting the pipe or an environment surrounding the pipe.

19. The robotic apparatus of claim 18, wherein the sensor assembly includes:

a sensor;

an arm member rotatably coupling the sensor to the robotic apparatus; and an actuator configured to rotate the arm member about the rotatable coupling to move the sensor towards or away from the pipe.

20. A method for navigating an obstacle on a pipe with a robotic apparatus, comprising:

providing a robotic apparatus comprising: (i) a first wheel configured for positioning on a first side of the pipe, (ii) a second wheel and a third wheel configured for positioning on a second, opposing side of the pipe, and (iii) a clamping mechanism connecting the first wheel to the second and third wheels, and situated offset from and parallel to a plane shared by the wheels so as to define an open side situated opposite the clamping mechanism;

advancing the robotic apparatus along a helical pathway on the pipe to position the open side of the robotic apparatus in longitudinal alignment with the obstacle on the pipe; and advancing the robotic apparatus along a straight pathway on the pipe such that the obstacle passes unobstructed through the open side of the robotic apparatus.

21. The method of claim 20, wherein advancing the robotic apparatus along a helical pathway includes adjusting an orientation of at least one of the wheels rotationally relative to an axis that is normal to the pipe.

22. The method of claim 20, wherein advancing the robotic apparatus along a straight pathway on the pipe includes adjusting an orientation of the wheels to be in alignment with a longitudinal axis of the pipe.

23. The method of claim 20, wherein the robotic apparatus includes one or more members configured to extend across the open side of the robotic apparatus to prevent the robotic apparatus from falling off the pipe, and wherein advancing the robotic apparatus along a straight pathway on the pipe such that the obstacle passes unobstructed through the open side of the robotic apparatus includes allowing the one or more members to pivot along a plane of the open side to accommodate passage of the obstacle through the open side of the robotic apparatus.

24. The method of claim 20, further including adjusting an orientation of two or more of the wheels in opposing directions to advance the robotic apparatus sideways relative to a longitudinal axis of the pipe and thereby reposition the robotic apparatus on the pipe to account for wheel slip.

* * * * *